US007332646B1

(12) United States Patent
Neuhold et al.

(10) Patent No.: US 7,332,646 B1
(45) Date of Patent: Feb. 19, 2008

(54) TRANSGENIC ANIMAL MODEL FOR DEGENERATIVE DISEASES OF CARTILAGE

(75) Inventors: Lisa Ann Neuhold, Princeton, NJ (US); Loran Marie Killar, Newtown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/717,450

(22) Filed: Nov. 20, 2000

Related U.S. Application Data

(63) Continuation of application No. 08/994,689, filed on Dec. 19, 1997, now Pat. No. 6,613,958.

(51) Int. Cl.
*A01K 67/00* (2006.01)
*C12P 15/00* (2006.01)
*G01N 33/00* (2006.01)

(52) U.S. Cl. .................... 800/14; 800/3; 800/8; 800/9; 800/15; 800/16; 800/17; 800/18; 800/21

(58) Field of Classification Search .................... 800/3, 800/8, 9, 13, 14–18, 21, 25
See application file for complete search history.

(56) References Cited

U.S. PATENT DOCUMENTS

| | | | | |
|---|---|---|---|---|
| 5,625,124 A | 4/1997 | Falk et al. | ...................... | 800/3 |
| 5,650,298 A | 7/1997 | Bujard et al. | .............. | 435/69.7 |
| 5,880,327 A | 3/1999 | Lubon et al. | ................... | 800/7 |
| 5,917,123 A | 6/1999 | McTiernan et al. | ............ | 800/18 |
| 6,028,245 A | 2/2000 | Wasylyk et al. | .............. | 800/18 |

FOREIGN PATENT DOCUMENTS

| | | |
|---|---|---|
| DE | 19501032 A | 7/1996 |
| WO | WO92/22333 | 6/1992 |
| WO | WO95/32285 A2 | 5/1995 |

OTHER PUBLICATIONS

Hammer et al. Spontaneous inflammatory disease in transgenic rats expressing HLA-B27 and human B2m: an animal model of HLA-B27-Associated human disorders Cell vol. 63, 1099-1112 Nov. 30, 1990.*
Taurog et al. HLA-B27 in inbred and non-inbred transgenic mice vol. 141,4020-4023 n0.11 Dec. 1, 1988.*
Mullins et al. Expression of the DBA/2J Ren-2 gene in the adrenal gland of transgenic mice vol. 8 No. 13 pp. 4065-4072 1989.*
Mullins et al. Fulminant hypertension in transgenic rats harbouring the mouse ren-2 gene Nature vol. 344 Apr. 5, 1990.*
Mullins et al. Perspectives Series: Molecular medicine in genetically engineered animals vol. 98, No. 11 1996 s37-s40.*
Niemann 1997, Transg. Res. vol. 7, p. 73-75.*
Mullins 1993, Hypertension, vol. 22, pp. 630-633.*
Cameron 1997, Molec. Biol., vol. 7, p. 253-265.*
Howland (PNAS, Feb. 5, 2002, vol. 99, No. 3, p. 1604-1609).*
Dietz and Sandell (1996) "Cloning of a Retinoic Acid-sensitive mRNA Expressed in Cartilage and during Chondrogenesis" *J. Biol. Chem.* 271:3311-16.

Bosserhoff et al. (1997) "Mouse CD-RAP/MIA Gene: Structure, Chromosomal Localization, and Expression in Cartilage and Chrondrosarcoma" *Dev. Dyn.* 208:516-25.
Zhou et al. (1995) "A 182 bp fragment of the mouse proα1(II) collagen gene is sufficient to direct chondrocyte expression in transgenic mice" *J. Cell. Sci.* 108:3677-84.
Goldring et al. (1994) "Interleukin-1β-modulated Gene Expression in Immortalized Human Chondrocytes" *J. Clin. Invest.* 94:2307-16.
McDougall et al. (1996) "Surface Adhesion-Medicated Regulation of Chondrocyte-Specific Gene Expression in the Nontransformed RCJ 3.1C5.18 Rat Chondrocyte Cell Line" *J. Bone Min. Res.* 11:1130-38.
Bosnakovski et al. (Feb. 9, 2006) "Chondrogenic Differentiation of Bovine Bone Marrow Mesenchymal Stem Cells (MSCs) in Different Hydrogels: Influence of Collagen Type II Extracellular Matrix on MSC Chondrogenesis" *Biotechnol. Bioeng.* [Epub ahead of print].
Doege et al. (1994) "The Structure of the Rat Aggrecan Gene and Preliminary Characterization of Its Promoter" *J. Biol. Chem.* 269:29232-40.
Watanabe et al. (1995) "Mouse aggrecan, a large cartilage protoglycan: protein sequence, gene structure and promoter sequence" *Biochem. J.* 308:433-40.
Xie et al. (1998) "Regulation of the Mouse Cartilage-derived Retinoic Acid-sensitive Protein Gene by the Transcription Factor AP-2" *J. Biol. Chem.* 273:5026-32.
Xie et al. (2000) "The 2.2-kb promoter of cartilage-derived retinoic acid-sensitive protein controls gene expression in cartilage and embryonic mammary buds of transgenic mice" *Matrix Biology* 19:501-09.
Perala et al. (1994) "The Exon Structure of the Mouse α2(IX) Collagen Gene Shows Unexpected Divergence from the Chick Gene" *J. Biol. Chem.* 269:5064-71.
Tsumaki et al. (1996) "Separable *cis*-regulatory Elements that Contribute to Tissue- and Site-specific α2(XI) Collagen Gene Expression in the Embryonic Mouse Cartilage" *J. Cell Biol.* 134:1573-82.
Deak et al. (1999) "Characterization and chromosome location of the mouse link protein gene (*Crtl 1*)" *Cytogenet. Cell Genet.* 87:75-79.
Rhodes et al. (1991) "Characterization of the promoter for the rat and human link protein gene" *Nuc. Acids Res.* 19:1933-39.
Issack et al. (2000) "Chondrocyte-specific Enhancer Regions in the COMP Gene" *J. Orthop. Res.* 18:345-50.

(Continued)

Primary Examiner—Michael C. Wilson
(74) Attorney, Agent, or Firm—Fitzpatrick, Cella, Harper & Scinto

(57) ABSTRACT

The present invention provides animal model systems for cartilage-degenerative disease, which comprise transgenic animals which can express recombinant matrix-degrading enzymes (MDEs), particularly matrix metalloproteinases (MMPs), in a temporally and spatially regulated manner. The invention also provides methods for producing phenotypic indicators of cartilage-degenerative disease in a mammal and methods for determining the potential of a composition to counteract cartilage-degenerative disease. The invention also provides isolated nucleic acids encoding proMMP polypeptides that exhibit constitutive enzymatic activity and isolated proMMP polypeptides.

41 Claims, 5 Drawing Sheets

OTHER PUBLICATIONS

Kanai and Koopman (1999) "Structural and functional characterization of the mouse Sox9 promoter: implications for campomelic dysplasia" *Hum. Mol. Genet.* 8:691-96.

Nauper, Vera, et al., "Biochemical Characterization of Human Collagenase-3", *The Journal of Biological Chemistry*, 271(3):1544-1550, Jan. 19, 1996.

Billinghurst, R. Clark, et al., "Enhanced Cleavage of Type II Collagen by Collagenases in Osteoarthritic Articular Cartilage", *J. Clin Invest.*, 99(7):1534-1545, Apr. 1997.

Mitchell, Peter G., et al., "Cloning, Expression, . . . Osteoarthritic Cartilage", *J. Clin. Invest.*, 97(3):761-768, Feb. 1996.

Liu, Xin, et al., "A Targeted Mutation at the Known . . . Remodeling", *The Journal of Cell Biology*, 130(1):227-237, Jul. 1995.

Khokha, Rama, et al., "Utilization of Transgenic Mice in the Study .. Inhibitors", *Cancer and Metastasis Reviews*, 14(2):97-111, 1995.

No, David, et al., "Ecdysone-Inducible Gene Expression in Mammalian Cells and Transgenic Mice", *Proc. Natl. Acad. Sci. USA*, 93:3346-3351, Apr. 1996.

Wang, Yaolin, et al., "A Regulatory System for Use in Gene Transfer", *Proc. Natl. Acad. Sci. USA*, 91:8180-8184, Aug. 1994.

Wang, Y., et al., "Positive and Negative Regulation of Gene Expression in Eukaryotic Cells with an Inducible Transcriptional Regulator", *Gene Therapy*, 4:432-441, 1997.

Mattioni, Tiziana, et al., "Regulation of Protein Activities by Fusion to Steroid Binding Domains", *Methods in Cell Biology*, 43:335-352, 1994.

Watson, James, D., et al., "The Introduction of Foreign Genes into Mice", *Recombinant DNA*, 2d Ed., W.H. Freeman & Co., New York, 1992, pp. 255-272.

Gordon, Jon W., "Transgenic Animals", *International Review of Cytology*, 155:171-229, 1989.

Jaenisch, Rudolf, "Transgenic Animals", *Science*, 240:1468-1474, Jun. 10, 1988.

Rossant, J., "Manipulating The Mouse Genome: Implications for Neurobiology", *Neuron*, 2:323-334, Mar. 1990.

Weingarten, Harold, et al., "Synthetic Substrates of Vertebrate Collagenase", *Biochemistry* 24:6730-6734, 1985.

Woessner, Jr., J. Frederick, and Taplin, C.J., "Purification and Properties of a Small Latent Matrix Metalloproteinase of the Rat Uterus", *The Journal of Biological Chemistry*, 263(14):16918-16925, Nov. 15, 1988.

Knight, C. Graham, et al., "A Novel Coumarin-Labelled Peptide . . . Metalloproteinases", *Federation of European Biochemical Societies Letters*, 296(3):263-266, Jan. 1992.

Witty, Jean, P., et al., "Matrix Metalloprteinases Are Expressed . . . Alveolar Development", *Molecular Biology of the Cell*, 6:1287-1303, Oct. 1995.

Gossen, Manfred, and Bujard, H., "Tight Control of Gene Expression in Mammalian . . . Promoters", *Proc. Natl. Acad. Sci. USA*, 89:5547-5551, Jun. 1992.

(Duplicate).

D'Armiento, Jeanine, et al., "Collagenase Expression in the Lungs of Transgenic Mice Causes Pulmonary Emphysema", *Cell*, 71: 995-961, Dec. 11, 1992.

Weir, Eleanor, C., et al., "Targeted Overexpression of . . . Bone Formation", *Proc. Natl. Acad. Sci. USA*, 93:10240-10245, Sep. 1996.

Overbeek, Paul A., "Transgenic Phenomenology", *Transgenic Animal Technology*, pp. 96-98.

Robl, James, M.,and Heideman, J.K., "Production of Transgenic Rats and Rabbits", *Transgenic Animal Technology*, pp. 265-270, 1994.

Mullins, Linda J., and Mullins, John J., "Perspectives Series: Molecular Medicine in Genetically Engineered Animals", *J. Clin. Invest.*, 98(11):S37-S40, 1996.

Shapiro, Steven, D., "Mighty Mice: Transgenic Technology 'Knocks out' Questions of Matrix Metalloproteinase", *Matrix Biology*, 15:527-533, 1997.

D'Armiento, Jeanine, et al., "Collagenase Expression in Transgenic Mouse Skin Causes . . . Tumorigenesis", *Molecular and Cellular Biology*, 15(15):5732-5739, Oct. 1995.

Freije, Jose M.P., et al., "Molecular Cloning and Expression of Collagenase-3, a Novel Human Matrix Metalloproteinase Produced by Breast Carcinomas", *The Journal of Biological Chemistry*, 269(24):16766-16773, Jun. 17, 1994.

Sympson, Carolyn J., et al., "Targeted Expression of Stromelysin-1 . . . Gene Expression", *The Journal of Cell Biology*, 125(3):681-693, May 1994.

Sanchez-Lopez, Rosana, et al., "Structure-Function Relationships in the Collagenase Family Member Transin", *The Journal of Biological Chemistry*, 263(24):11892-11900, Aug. 1988.

Kozaci, L. Didem, et al., "Degradation of Type II Collagen, . . . Cultures", *Arthritis & Rheumatism*, 40(1):164-174, Jan. 1997.

Wall, R.J., "Transgenic Livestock: Progress and Prospects for the Future", *Theriogenology*, 45:57-68, 1996.

Ebert, Karl M. et al., "A Moloney MLV-Rat Somatotropin Fusion Gene Produces Biologically Active Somatotropin in a Transgenic Pig", *Molecular Endocrinology*, pp. 277-282, 1988.

Knauper et al. (1997) "The Role of the C-terminal Domain of Human Collagenase-3 (MMP-13) in the Activation of Procollagenase-3, Substrate Specificity, and Tissue Inhibitor of Matalloproteinase interaction" J. Biol. Chem. 272:7608-16.

Allgood and Eastman (1997) "Chimeric Receptors as Gene Switches" Curr. Opinion Biotech. 8:474-79.

Bradley and Liu (1996) "Target Practice in Transgenics" Nature Genetics 14:121-23.

Burcin et al. (1999) "Adenovirus-Mediated Regulable Target Gene Expression *in vivo* " Proc. Natl. Acad. Sci. USA 96:335-60.

Feil et al. (1996) "Ligand-Activated Site-Specific Recombination in Mice" Proc. Natl. Acad. Sci. USA 93:10887-90.

Gossen et al. (1995) "Transcriptional Activation by Tetracyclines in Mammalian Cells" Science 268:1766-69.

Shockett and Schatz (1996) "Diverse Strategies for Tetracycline-Regulated Inducible Gene Expression" Proc. Natl. Acad. Sci. USA 93:5173-76.

Shockett and Schatz (1997) "Switching on Gene Expression" Nature Biotech. 15:220-21.

Wang et al. (1997) "Ligand-Inducible and Liver-Specific Target Gene Expression in Transgenic Mice" Nature Biotech. 15:239-43.

Pirok et al. (1997) "Structural and Functional Analysis if the Chick Chondroitin Sulfate Proteoglycan (Aggrecan) Promoter and Enhancer Region" J. Biol. Chem. 272:11566-74.

Lefebvre et al. (1998) "A New Long Lorm of Sox5 (L-Sox 5), Sox6 and Sox9 are Coexpressed in Chondrogenesis and Cooperatively Activate the Type II Collagen Gene" EMBO J. 17:5718-33.

Apte et al. (1997) "The Matrix Metalloproteinase-14 (MMP-14) Gene Is Structurally Distinct From Other MMP Genes and Is Co-expressed with the TIMP-2 Gene During Mouse Embryogenesis" J. Biol. Chem. 272:25511-17.

Masure et al. (1997) "Production and Characterization of Recombinant Active Mouse Gelatinase B from Eukaryotic Cells and *in vivo* Effects after Intravenous Adminstration" Eur. J. Biochem. 244:21-30.

Matsumoto et al. (1997) "Identification of Soluble Type of Membrane-Type Matrix Metalloproteinase-3 Formed by Alternatively Spliced mRNA" Biochim. Biophys. Acta. 1354:159-70.

Wang et al. (1991) "Identification of a *cis*-Acting Sequence in the Collagen II Enhancer Required for Chondrocyte Expression and the Binding of a Chondrocyte nuclear Factor. "J. Biol. Chem. 266:19878-81.

Vikkula et al. (1992) "Structural Analysis of the Regulatory Elements of the Type-II Procollagen gene. Conservation of Promoter and First Intron sequences Between Human and Mouse" Biochem J. 285:287-94.

Overbeek, Paul A., "Transgenic Phenomenology", *Transgenic Animal Technology*, pp. 96-98 1994.

Robl, James, M., and Heideman, J.K., "Production of Transgenic Rats and Rabbits", *Transgenic Animal Technology*, pp. 265-270, 1994.

Mullins, Linda J., and Mullins, John J., "Perspectives Series: Molecular Medicine in Genetically Engineered Animals", *J. Clin. Invest.*, 98(11):S37-S40, 1996.

Shapiro, Steven, D., "Mighty Mice: Transgenic Technology 'Knocks out 'Questions of Matrix Metalloproteinase", *Matrix Biology*, 15:527-533, 1997.

D'Armiento, Jeanine, et al., "Collagenase Expression in Transgenic Mouse Skin Causes... Tumorigenesis", *Molecular and Cellular Biology*, 15(15):5732-5739, Oct. 1995.

Freije, Jose M.P., et al., "Molecular Cloning and Expression of Collagenase-3, a Novel Human Matrix Metalloproteinase Producted by Breast Carcinomas", *The Journal of Biological Chemistry*, 269(24):16766-16773, Jun. 17, 1994.

Sympson, Carolyn J., et al., "Targeted Expression of Stromelysin-1 ... Gene Expression", *The Journal of Cell Biology*, 125(3):681-693, May 1994.

Sanchez-Lopez, Rosana, et al., "Structure-Function Relationships in the Collagenase Family Member Transin", *The Journal of Biological Chemistry*, 263(24):11892-11900, Aug. 1988.

Kozaci, L. Didem, et al., "Degradation of Type II Collagen, ... Cultyres", *Arthritis & Rheumatism*, 40(1):164-174, Jan. 1997.

Wall, R. J., "Transgenic Livestock: Progress and Prospects for the Future", *Theriogenology*, 45:57-68, 1996.

Ebert, Karl M. et al., "A Molobey MLV-Rat Somatotropin Fusion Gene Produces Biologically Active Somatotropin in a Transgenic Pig", *Molecular Endocrinology*, pp. 277-282, 1988.

Gack et al. (1994) "Phenotypic Alterations in Fos-transgenic Mice Correlate with Chenges in Fos/Jun-dependent Collagenase Type I Expression, "J. Biol. Chem. 269:10363-9.

Sympson, C.J. et al, *Cell Biology*, 125(3):681-693, May 1994.

Sanchez-Lopez, R. et al, *J. Biol. Chem.* 263(24):11892-11899, Aug. 25, 1988.

Kozaci, L. et al, *Arthritis Rheum.* 40(1):164-174, Jan. 1997.

Wang et al, *Gene Therapy* 4:432, 1997.

Mattioni et al, *Meth. Cell Biol.* 43:335, 1994.

Watson et al, "The Introduction of Foreign Genes Into Mice, "in *Recombinant DNA*, 2d Ed., W. H. Freeman & Co., New York, 1992, pp. 255-272.

Gordon, J. W., *Int. Rev. Cytol.* 115:171, 1989.

Jaenisch, *Science* 240:1463, 1989.

Rossant, *Neuron* 2:323, 1990.

Weingarten et al, *Biochem.* 24:6730, 1985.

Woessner et al, *J. Biol. Chem.* 263:16918, 1988.

Knight et al, *FEBS* Letts., 296:263, 1992.

Witty, J. P. et al, *Mol. Biol. Of the Cell*, 6:1287, Oct. 1995.

Gossen et al, *Proc. Natl. Acad. Sci.* USA 89:5547, 1992.

D'Armiento, J. et al, *Cell*, 71:955-961, Dec. 11, 1992.

Weir, E.C. et al, *Proc. Natl. Acad. Sci.* USA, 93:10240-10245, Sep. 1996.

\* cited by examiner

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 471 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met His Pro Gly Val Leu Ala Ala Phe Leu Phe Leu Ser Trp Thr His
 1               5                  10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
        35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95
```

```
Gly Val Val Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
            115                 120                 125

Met Thr His Ser Glu Val Glu Lys Ala Phe Lys Ala Phe Lys Val
            130                 135                 140

Trp Ser Asp Val Thr Pro Leu Asn Phe Thr Arg Leu His Asp Gly Ile
145                     150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
                180                 185                 190

Pro Asn Tyr Gly Gly Asp Ala His Phe Asp Asp Glu Thr Trp Thr
                195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
                260                 265                 270

Pro Asn Pro Lys His Pro Lys Thr Pro Asp Lys Cys Asp Pro Ser Leu
        275                 280                 285

Ser Leu Asp Ala Ile Thr Ser Leu Arg Gly Glu Thr Met Ile Phe Lys
    290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
                340                 345                 350

Lys Phe Trp Ala Leu Asn Gly Tyr Asp Ile Leu Glu Gly Tyr Pro Lys
                355                 360                 365

Lys Ile Ser Glu Leu Gly Leu Pro Lys Glu Val Lys Lys Ile Ser Ala
    370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
                420                 425                 430

Ala Val Tyr Glu Lys Asn Gly Tyr Ile Tyr Phe Phe Asn Gly Pro Ile
                435                 440                 445

Gln Phe Glu Tyr Ser Ile Trp Ser Asn Arg Ile Val Arg Val Met Pro
    450                 455                 460

Ala Asn Ser Ile Leu Trp Cys
465                 470
```

(2) INFORMATION FOR SEQ ID NO: 2:

(i) SEQUENCE CHARACTERISTICS:
        (A) LENGTH: 470 base pairs
        (B) TYPE: nucleic acid
        (C) STRANDEDNESS: single (D) TOPOLOGY: linear (xi) SEQUENCE DESCRIPTION: SEQ ID NO: 2:

| | | | | | |
|---|---|---|---|---|---|
| CTCGAGTTTA | CCACTCCCTA | TCAGTGATAG | AGAAAAGTGA | AAGTCGAGTT | TACCACTCCC | 60 |
| TATCAGTGAT | AGAGAAAAGT | GAAAGTCGAG | TTTACCACTC | CCTATCAGTG | ATAGAGAAAA | 120 |
| GTGAAAGTCG | AGTTTACCAC | TCCCTATCAG | TGATAGAGAA | AAGTGAAAGT | CGAGTTTACC | 180 |
| ACTCCCTATC | AGTGATAGAG | AAAGTGAAA | GTCGAGTTTA | CCACTCCCTA | TCAGTGATAG | 240 |
| AGAAAAGTGA | AGTCGAGTT | TACCACTCCC | TATCAGTGAT | AGAGAAAAGT | GAAAGTCGAG | 300 |
| CTCGGTACCC | GGGTCGAGTA | GGCGTGTACG | GTGGGAGGCC | TATATAAGCA | GAGCTCGTTT | 360 |
| AGTGAACCGT | CAGATCGCCT | GGAGACGCCA | TCCACGCTGT | TTTGACCTCC | ATAGAAGACA | 420 |
| CCGGGACCGA | TCCAGCCTCC | GCGGCCCCGA | ATTAGCTTGA | TATCGAATTC | | 470 |

(2) INFORMATION FOR SEQ ID NO: 3:

(i) SEQUENCE CHARACTERISTICS:
        (A) LENGTH: 3479 base pairs
        (B) TYPE: nucleic acid
        (C) STRANDEDNESS: single
        (D) TOPOLOGY: linear (xi) SEQUENCE DESCRIPTION: SEQ ID NO: 3:

| | | | | | |
|---|---|---|---|---|---|
| GGTACCACTA | GTAAGCTTAG | ATCCACTGTC | TGGGATTATA | TCAGGACAAC | CGAAGCCTGG | 60 |
| AAAGTGTATT | AGGTAGAGCA | TTTTCTTCCA | CGTGTTTGGG | CACGTTTCCG | ACAGCTAGGA | 120 |
| TTCCAGCTCT | GTCTTTGTAT | GTTACAGACT | GTAAATCAAT | CGCAGGTGAA | ACTGTTTGGA | 180 |
| CAGTAGGTGG | GGATCAAAGA | CCCTCCGCCC | GTGAGACTCT | AGGCGCTTTC | CCCTGCCACC | 240 |
| AGCCTGTCTC | CAGAGATGCT | CTGGAAGGAG | GCGGGCCCGG | GCGGTCTTTC | TGCTCTTTAG | 300 |
| CGTGGCGGAC | GCGGCGGCGG | GGGCAGGGCT | GGAGCAGAGA | GCGCTGCAGT | GATAGAACTT | 360 |
| TCTGACCCCG | CTGCGCAGGG | CGGCAGGGTG | GCAGGGTGGC | AGGGTGGCGA | GCTAAGCCAG | 420 |
| AGCCGAACGC | TGGAGCTCTG | GGAGGAACAT | CGAAGGTTTG | TATGTGGTCT | GAGATCGGCC | 480 |
| TGACTATATT | TTTTTGTCCT | AAATTTGCAA | GCACACACCC | ACAAAGCTGC | GGTCTTGACC | 540 |
| GGTATTCTTT | ATAGAGCGCA | ATGGAGTGAG | CTGAGTGTCT | AAACGATTTC | CCTAATTCAT | 600 |
| CTGATAGCAG | AGGCGCTCTC | CTAATTGGCG | AAGAGCTGCC | TCATGTCCGC | AACTTTTTGG | 660 |
| CAGAGTGAAT | TCCACAGCTT | TGTGTGTGTG | TGTGGGGGG | GGTGTAAGGG | GTGTCTAAAA | 720 |
| CTTTCGGTCT | CCTACTATTC | TGTATCTCGA | CCGGTTGGTT | TTACACCCCG | GCTCATCTCA | 780 |
| TCAACGCAAA | CACCCCCACT | CTCCTATGGA | CCCAAGGACC | TGACGTGGGG | GAAGGTGGAC | 840 |
| ATTAGGAATG | TCAGAAACCT | AGAGTCCACG | CTCCTCCTCT | CCATCTTTCC | ACGAGTTTGG | 900 |
| GAAACTTCTT | GGCTGCGAAG | ACTTTGACCC | ACATCTGCAT | TTCTCAGCCC | CAGCTTCCAA | 960 |
| AAGTGCTGCA | GGTTCGGGAG | GGGAGACCTC | AGTCCTCCTT | TGTGAGGCTT | GTTTGCGTTG | 1020 |
| AGGGATTGGC | AGCGATGGCT | TCCAGATGGG | CTGAAACCCT | GCCCGTATTT | ATTTAAACTG | 1080 |
| GTTCCTCGTG | GAGAGCTGTG | AATCGGGCTC | TGTATGCGCT | CGAGAAAAGC | CCCATTCATG | 1140 |
| AGAGGCAAGG | CCCAGTGGGT | CCCCCCGACT | CCCCGACCCC | CCTCTCCCAC | AATATATCCC | 1200 |
| CCCTCCCTGT | GCCCGCCTGC | CGCCACCTCC | CGGGCTCCGG | CCCCGCGCGC | AGCGGCGACG | 1260 |
| AAGCAACACA | GTTCCCCGAA | AGAGGTAGCT | TTTTAATTGG | CCAGCCACAA | AGAATCACTT | 1320 |
| ATGCCGCACG | GCGGTAACGA | GGGGAACCGG | ATCGGGCGGC | CAGGATGCTA | TCTGTGTAGC | 1380 |
| CCTTTTCGTG | CCACAATTAG | GGTGGTGCTG | GCTTCCTCCG | ACCGCACCTA | GGCGATCTGG | 1440 |

```
TTACACTGTT GGCTCCTTTC TTGGGCAGTC ATTTAATCCT ACTTTTTACT CTACGAATGT    1500

CTGTCTGATG GAGGGCTGTG TCCGGAGCCC CATCCACAAA GAGTCAGCCA GCAGCTCTCA    1560

CACCCGGCTG GATCTCATAT GGTGCACTCT CAGTACAATC TGCTCTGATG CCGCATAGTT    1620

AAGCCAGCCA AGCTAGCTTG CGCAAGCTAG CTTGCGATCC GTAAAAATGT GTGAGAGTTA    1680

CAAAATGTCT TCCGGGCTAA GATCCGACAG CCATGGTCCA AGAAGACTT CGGCACTGCA     1740

GACTTAAAAC CAGCTTTCTA GCAGAGGCAG AAGGATCTAG AGCCAAAGGC AAAGACTTGA    1800

ATAGGCTGGG AAGATGCAAG AATGGCATTT TACATAAAGA ACACTCTCTC CTTTTCCAGC    1860

CAGCACACTT GCATAGAAAT TAAGTTTTAC ACTTGAAGTT CTTTGTTTCC ATCCTGAGAA    1920

GCTCCAAAGT CTGAGGTGGT GTGGTATGCT GGGTAATTCT CCCCACCCCC CAACATTCCC    1980

TGGGGGTTCC ATGGGGGTAG CTTCTCCCAA GGACTTCCAG CGGCAACACA GAAATCCCAC    2040

TTCGAGACAA AGGAGTTACT GCTTAAATCA GGCCCTAATT TCCAAGGTTC CCTTTGCTTA    2100

AAGTTCCCTA GAGGACCATC TCACTTCTAA AGAAAAGGTG TATTCGGGGA CCCATCCTCA    2160

ACCTCCTTGT TATGGAAGGA GACTTCGGGA ACAGAGCAAG GGCTGAGCCT CCGGCAGTTT    2220

GGGGTAAGGT TGGGGTTGGG GGGAGCAAGG AAGGCAAGTG AGGCTGGAGG CCCAGGGATA    2280

GGGGAAGATG TGTGTGTGTG TGTGTGTGTG TGTGTGTGTG TGTGTGTGTC TCGGGGATGG    2340

TGGTGGTGGA CAACTAGGAA ACTCTGGCGC TTTCTCCTCC CCTCACAAAA CTGAGTCCAG    2400

CTGGAGCCGC CTCCAGACTC TCTGGCCAGG GCCTCAGAGT GGTCAACAGT CCCTGGCCAG    2460

CGTTGCTCTC TCCAGGCTAA GGGCACCCAC TCCCCTGGAG ATTCCTGAAC CTGGGCCAGG    2520

AAGAGCCGAA TTAGACAAGT GTCTCCAATC CGGCTGCGTG CGGATTTTGT TGCGGTGTCC    2580

CTCGGTTGTC TGCAGTTCCT TTAGTCCCTT CCCTGGCCTG CCCCTTACAC CTCCACACAG    2640

GTCCCCCTCT GTGTAGGAAT ACACCAGACC CTCTCTTAGC CACACACACC TCCAGTCCCC    2700

CGTCTACCTA GATTTTTTTC ATAGCTAGTT GGATGGGGA TGGGTTAGGG AGGCTGGGTT     2760

TGCGAGCCTC CAGGTGGGAG TTCACCGACA GGTACTCCGC AAAGGAGCTG GAAGGCAGGT    2820

CTGGAAAACT GTCCCCCAGA TTTAGGATTC TGGGCAGCTT CCATCAGCTT ATACTTTGGC    2880

TCCCCCGCCC CCTAAACTCC CCATCCCCAC CTTCCTTTCT CCCGTTACTT CGTCCTCCCT    2940

CGCCTTTCCA GCCTTGAGTC TAAAGCTCCA TGCTTATGCC TCTGCAAACA ACCCCCTCCC    3000

TTCTAACCCC AGCAGAACTC CGAGGAAAGG GGCCGGAGGC CCCCCTTCTC GCCTGTGGTT    3060

AGAGGGGGCA GTGTGGCAGT CCCAAGTGGG GGCGACCGGA GGCCGTCTCG GTGCCCCGCC    3120

CGATCAGGCC ACTGGGCACA TCGGGGGCGG GAAGCTGGGC TCACCAAAGG GGCGACTGGC    3180

CTTGGCAGGT GTGGGCTCTG GTCCGGCCTG GGCAGGCTCC GGGGGCGGGG TCTCAGGTTA    3240

CAGCCCCGCG GGGGGCTGGG GGGCGGCCCG CGGTTTGGGC TGGTTTGCCA GCCTTTGGAG    3300

CGACCGGGAG CATATAACCG GAGCCTCTGC TGGGAGAAGA CGCAGAGCGC CGCTGGGCTG    3360

CCGGGTCTCC TGCCTCCTCC TCCTGCTCCT AGAGCCTCCT GCATGAGGGC GCGGTAGAGA    3420

CCCGGACCCG CTCCGTGCTC TGCCGCCTCG CCGAGCTTCG CCCGCAAGCT GGGGAATTC     3479
```

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Pro Arg Cys Gly Val Pro Asp Val
 1               5

(2) INFORMATION FOR SEQ ID NO: 5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 5:

```
AAGCCAAGAT GCGGGGTTGT CGATGTGGGT GAATACAAT                              39
```

(2) INFORMATION FOR SEQ ID NO: 6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 6:

```
GAAAAAGCCA AGATGCGGGG GTCCTGATGT GGGTGAATAC                             40
```

(2) INFORMATION FOR SEQ ID NO: 7:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO: 7:

```
GGTACCACTA GTAAGCTTAG ATCTCATATG GTCGACCCCG GGGAATTCCT GCAGGGATCC       60

TCTAGAAGTA CTCCATGGGT ATACATCGAT GCGGCCGC                               98
```

(2) INFORMATION FOR SEQ ID NO: 8:

(i) SEQUENCE CHARACTERISTICS:
        (A) LENGTH: 2792 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
CTCGAGTTTA CCACTCCCTA TCAGTGATAG AGAAAAGTGA AAGTCGAGTT TACCACTCCC       60

TATCAGTGAT AGAGAAAAGT GAAAGTCGAG TTTACCACTC CCTATCAGTG ATAGAGAAAA      120

GTGAAAGTCG AGTTTACCAC TCCCTATCAG TGATAGAGAA AAGTGAAAGT CGAGTTTACC      180

ACTCCCTATC AGTGATAGAG AAAGTGAAA GTCGAGTTTA CCACTCCCTA TCAGTGATAG       240

AGAAAAGTGA AAGTCGAGTT TACCACTCCC TATCAGTGAT AGAGAAAAGT GAAAGTCGAG      300

CTCGGTACCC GGGTCGAGTA GGCGTGTACG GTGGGAGGCC TATATAAGCA GAGCTCGTTT      360

AGTGAACCGT CAGATCGCCT GGAGACGCCA TCCACGCTGT TTTGACCTCC ATAGAAGACA      420

CCGGGACCGA TCCAGCCTCC GCGGCCCCGA ATTAGCTTGA TATCGAATTC GAGCTCGGTA      480

CCCGGGGATC CTCTAGACAA GATGCATCCA GGGGTCCTGG CTGCCTTCCT CTTCTTGAGC      540

TGGACTCATT GTCGGGCCCT GCCCCTTCCC AGTGGTGGTG ATGAAGATGA TTTGTCTGAG      600
```

-continued

```
GAAGACCTCC AGTTTGCAGA GCGCTACCTG AGATCATACT ACCATCCTAC AAATCTCGCG      660

GGAATCCTGA AGGAGAATGC AGCAAGCTCC ATGACTGAGA GGCTCCGAGA AATGCAGTCT      720

TTCTTCGGCT TAGAGGTGAC TGGCAAACTT GACGATAACA CCTTAGATGT CATGAAAAAG      780

CCAAGATGCG GGGTTGTCGA TGTGGGTGAA TACAATGTTT TCCCTCGAAC TCTTAAATGG      840

TCCAAAATGA ATTTAACCTA CAGAATTGTG AATTACACCC CTGATATGAC TCATTCTGAA      900

GTCGAAAAGG CATTCAAAAA AGCCTTCAAA GTTTGGTCCG ATGTAACTCC TCTGAATTTT      960

ACCAGACTTC ACGATGGCAT TGCTGACATC ATGATCTCTT TTGGAATTAA GGAGCATGGC      1020

GACTTCTACC CATTTGATGG GCCCTCTGGC CTGCTGGCTC ATGCTTTTCC TCCTGGGCCA      1080

AATTATGGAG GAGATGCCCA TTTTGATGAT GATGAAACCT GGACAAGTAG TTCCAAAGGC      1140

TACAACTTGT TCTTGTTGC TGCGCATGAG TTCGGCCACT CCTTAGGTCT TGACCACTCC       1200

AAGGACCCTG GAGCACTCAT GTTTCCTATC TACACCTACA CCGGCAAAAG CCACTTTATG      1260

CTTCCTGATG ACGATGTACA AGGGATCCAG TCTCTCTATG GTCCAGGAGA TGAAGACCCC      1320

AACCCTAAAC ATCCAAAAAC GCCAGACAAA TGTGACCCTT CCTTATCCCT TGATGCCATT      1380

ACCAGTCTCC GAGGAGAAAC AATGATCTTT AAAGACAGAT TCTTCTGGCG CCTGCATCCT      1440

CAGCAGGTTG ATGCGGAGCT GTTTTTAACG AAATCATTTT GGCCAGAACT TCCCAACCGT      1500

ATTGATGCTG CATATGAGCA CCCTTCTCAT GACCTCATCT TCATCTTCAG AGGTAGAAAA      1560

TTTTGGGCTC TTAATGGTTA TGACATTCTG GAAGGTTATC CCAAAAAAAT ATCTGAACTG      1620

GGTCTTCCAA AAGAAGTTAA AAAGATAAGT GCAGCTGTTC ACTTTGAGGA TACAGGCAAG      1680

ACTCTCCTGT TCTCAGGAAA CCAGGTCTGG AGATATGATG ATACTAACCA TATTATGGAT      1740

AAAGACTATC CGAGACTAAT AGAAGAAGAC TTCCCAGGAA TTGGTGATAA AGTAGATGCT      1800

GTCTATGAGA AAAATGGTTA TATCTATTTT TTCAACGGAC CCATACAGTT TGAATACAGC      1860

ATCTGGAGTA ACCGTATTGT TCGCGTCATG CCAGCAAATT CCATTTTGTG GTGTTAAGTG      1920

TCTTTTTAAA AATTGTTATT TAAATCCTGA AGAGCATTTG GGGTAATACT TCCAGAAGTG      1980

CGGGGTAGGG GAAGAAGAGC TATCAGGAGA AAGCTCTAGT TCTAGAGGGC CCTATTCTAT      2040

AGTGTCACCT AAATGCTAGA GGATCTTTGT GAAGGAACCT TACTTCTGTG GTGTGACATA      2100

ATTGGACAAA CTACCTACAG AGATTTAAAG CTCTAAGGTA AATATAAAAT TTTTAAGTGT      2160

ATAATGTGTT AAACTACTGA TTCTAATTGT TTGTGTATTT TAGATTCCAA CCTATGGAAC      2220

TGATGAATGG GAGCAGTGGT GGAATGCCTT TAATGAGGAA AACCTGTTTT GCTCAGAAGA      2280

AATGCCATCT AGTGATGATG AGGCTACTGC TGACTCTCAA CATTCTACTC CTCCAAAAAA      2340

GAAGAGAAAG GTAGAAGACC CCAAGGACTT TCCTTCAGAA TTGCTAAGTT TTTTGAGTCA      2400

TGCTGTGTTT AGTAATAGAA CTCTTGCTTG CTTTGCTATT TACACCACAA AGGAAAAAGC      2460

TGCACTGCTA TACAAGAAAA TTATGGAAAA ATATTTGATG TATAGTGCCT TGACTAGAGA      2520

TCATAATCAG CCATACCACA TTTGTAGAGG TTTTACTTGC TTTAAAAAAC CTCCCACACC      2580

TCCCCCTGAA CCTGAAACAT AAAATGAATG CAATTGTTGT TGTTAACTTG TTTATTGCAG      2640

CTTATAATGG TTACAAATAA AGCAATAGCA TCACAAATTT CACAAATAAA GCATTTTTTT      2700

CACTGCATTC TAGTTGTGGT TTGTCCAAAC TCATCAATGT ATCTTATCAT GTCTGGATCA      2760

TCCCGCCATG GGTATACATC GATGCGGCCG CC                                   2792
```

(2) INFORMATION FOR SEQ ID NO: 9:

(i) SEQUENCE CHARACTERISTICS:
        (A) LENGTH: 5276 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 9:

```
GGTACCACTA GTAAGCTTAG ATCCACTGTC TGGGATTATA TCAGGACAAC CGAAGCCTGG      60
AAAGTGTATT AGGTAGAGCA TTTTCTTCCA CGTGTTTGGG CACGTTTCCG ACAGCTAGGA     120
TTCCAGCTCT GTCTTTGTAT GTTACAGACT GTAAATCAAT CGCAGGTGAA ACTGTTTGGA     180
CAGTAGGTGG GGATCAAAGA CCCTCCGCCC GTGAGACTCT AGGCGCTTTC CCCTGCCACC     240
AGCCTGTCTC CAGAGATGCT CTGGAAGGAG GCGGGCCCGG GCGGTCTTTC TGCTCTTTAG     300
CGTGGCGGAC GCGGCGGCGG GGGCAGGGCT GGAGCAGAGA GCGCTGCAGT GATAGAACTT     360
TCTGACCCCG CTGCGCAGGG CGGCAGGGTG GCAGGGTGGC AGGGTGGCGA GCTAAGCCAG     420
AGCCGAACGC TGGAGCTCTG GGAGGAACAT CGAAGTGTTT GTATGTGGTC TGAGATCGGC     480
CTGACTATAT TTTTTTGTCC TAAATTTGCA AGCACACACC CACAAAGCTG CGGTCTTGAC     540
CGGTATTCTT TATAGAGCGC AATGGAGTGA GCTGAGTGTC TAAACGATTT CCCTAATTCA     600
TCTGATAGCA GAGGCGCTCT CCTAATTGGC GAAGAGCTGC CTCATGTCCG CAACTTTTTG     660
GCAGAGTGAA TTCACAGCT TTGTGTGTGT GTGTGGGGG GGGTGTAAGG GGTGTCTAAA      720
ACTTTCGGTC TCCTACTATT CTGTATCTCG ACCGGTTGGT TTTACACCCC GGCTCATCTC     780
ATCAACGCAA ACACCCCCAC TCTCCTATGG ACCCAAGGAC CTGACGTGGG GGAAGGTGGA     840
CATTAGGAAT GTCAGAAACC TAGAGTCCAC GCTCCTCCTC TCCATCTTTC CACGAGTTTG     900
GGAAACTTCT TGGCTGCGAA GACTTTGACC CACATCTGCA TTTCTCAGCC CCAGCTTCCA     960
AAAGTGCTGC AGGTTCGGGA GGGGAGACCT CAGTCCTCCT TTGTGAGGCT TGTTTGCGTT    1020
GAGGGATTGG CAGCGATGGC TTCCAGATGG GCTGAAACCC TGCCCGTATT TATTTAAACT    1080
GGTTCCTCGT GGAGAGCTGT GAATCGGGCT CTGTATGCGC TCGAGAAAAG CCCCATTCAT    1140
GAGAGGCAAG GCCCAGTGGG TCCCCCCGAC TCCCCGACCC CCTCTCCCA CAATATATCC     1200
CCCCTCCCTG TGCCCGCCTG CCGCCACCTC CCGGGCTCCG GCCCCGCGCG CAGCGGCGAC    1260
GAAGCAACAC AGTTCCCCGA AAGAGGTAGC TTTTTAATTG GCCAGCCACA AAGAATCACT    1320
TATGCCGCAC GGCGGTAACG AGGGGAACCG GATCGGGCGG CCAGGATGCT ATCTGTGTAG    1380
CCCTTTTCGT GCCACAATTA GGGTGGTGCT GGCTTCCTCC GACCGCACCT AGGCGATCTG    1440
GTTACACTGT TGGCTCCTTT CTTGGGCAGT CATTTAATCC TACTTTTTAC TCTACGAATG    1500
TCTGTCTGAT GGAGGGCTGT GTCCGGAGCC CCATCCACAA AGAGTCAGCC AGCAGCTCTC    1560
ACACCCGGCT GGATCTCATA TGGTGCACTC TCAGTACAAT CTGCTCTGAT GCCGCATAGT    1620
TAAGCCAGCC AAGCTAGCTT GCGCAAGCTA GCTTGCGATC CGTAAAAATG TGTGAGAGTT    1680
ACAAAATGTC TTCCGGGCTA AGATCCGACA GCCATGGTCC AAAGAAGACT TCGGCACTGC    1740
AGACTTAAAA CCAGCTTTCT AGCAGAGGCA GAAGGATCTA GAGCCAAAGG CAAAGACTTG    1800
AATAGGCTGG GAAGATGCAA GAATGGCATT TTACATAAAG AACACTCTCT CCTTTTCCAG    1860
CCAGCACACT TGCATAGAAA TTAAGTTTTA CACTTGAAGT TCTTTGTTTC CATCCTGAGA    1920
AGCTCCAAAG TCTGAGGTGG TGTGGTATGC TGGGTAATTC TCCCCACCCC CCAACATTCC    1980
CTGGGGGTTC CATGGGGGTA GCTTCTCCCA AGGACTTCCA GCGGCAACAC AGAAATCCCA    2040
CTTCGAGACA AAGGAGTTAC TGCTTAAATC AGGCCCTAAT TTCCAAGGTT CCCTTTGCTT    2100
AAAGTTCCCT AGAGGACCAT CTCACTTCTA AAGAAAAGGT GTATTCGGGG ACCCATCCTC    2160
```

-continued

```
AACCTCCTTG TTATGGAAGG AGACTTCGGG AACAGAGCAA GGGCTGAGCC TCCGGCAGTT    2220

TGGGGTAAGG TTGGGGTTGG GGGGAGCAAG GAAGGCAAGT GAGGCTGGAG GCCCAGGGAT    2280

AGGGGAAGAT GTGTGTGTGT GTGTGTGTGT GTGTGTGTGT GTGTGTGTGT CTCGGGGATG    2340

GTGGTGGTGG ACAACTAGGA AACTCTGGCG CTTTCTCCTC CCCTCACAAA ACTGAGTCCA    2400

GCTGGAGCCG CCTCCAGACT CTCTGGCCAG GGCCTCAGAG TGGTCAACAG TCCCTGGCCA    2460

GCGTTGCTCT CTCCAGGCTA AGGGCACCCA CTCCCCTGGA GATTCCTGAA CCTGGGCCAG    2520

GAAGAGCCGA ATTAGACAAG TGTCTCCAAT CCGGCTGCGT GCGGATTTTG TTGCGGTGTC    2580

CCTCGGTTGT CTGCAGTTCC TTTAGTCCCT TCCCTGGCCT GCCCCTTACA CCTCCACACA    2640

GGTCCCCCTC TGTGTAGGAA TACACCAGAC CCTCTCTTAG CCACACACAC CTCCAGTCCC    2700

CCGTCTACCT AGATTTTTTT CATAGCTAGT TGGATGGGGG ATGGGTTAGG GAGGCTGGGT    2760

TTGCGAGCCT CCAGGTGGGA GTTCACCGAC AGGTACTCCG CAAAGGAGCT GGAAGGCAGG    2820

TCTGGAAAAC TGTCCCCCAG ATTTAGGATT CTGGGCAGCT TCCATCAGCT TATACTTTGG    2880

CTCCCCCGCC CCCTAAACTC CCCATCCCCA CCTTCCTTTC TCCCGTTACT TCGTCCTCCC    2940

TCGCCTTTCC AGCCTTGAGT CTAAAGCTCC ATGCTTATGC CTCTGCAAAC AACCCCCTCC    3000

CTTCTAACCC CAGCAGAACT CCGAGGAAAG GGGCCGGAGG CCCCCCTTCT CGCCTGTGGT    3060

TAGAGGGGGC AGTGTGGCAG TCCCAAGTGG GGGCGACCGG AGGCCGTCTC GGTGCCCCGC    3120

CCGATCAGGC CACTGGGCAC ATCGGGGCG GGAAGCTGGG CTCACCAAAG GGGCGACTGG    3180

CCTTGGCAGG TGTGGGCTCT GGTCCGGCCT GGGCAGGCTC CGGGGCGGG GTCTCAGGTT    3240

ACAGCCCCGC GGGGGGCTGG GGGGCGGCCC GCGGTTTGGG CTGGTTTGCC AGCCTTTGGA    3300

GCGACCGGGA GCATATAACC GGAGCCTCTG CTGGGAGAAG ACGCAGAGCG CCGCTGGGCT    3360

GCCGGGTCTC CTGCCTCCTC CTCCTGCTCC TAGAGCCTCC TGCATGAGGG CGCGGTAGAG    3420

ACCCGGACCC GCTCCGTGCT CTGCCGCCTC GCCGAGCTTC GCCCGCAAGC TGGGGAATTC    3480

ATATGTCTAG ATTAGATAAA AGTAAAGTGA TTAACAGCGC ATTAGAGCTG CTTAATGAGG    3540

TCGGAATCGA AGGTTTAACA ACCCGTAAAC TCGCCCAGAA GCTAGGTGTA GAGCAGCCTA    3600

CATTGTATTG GCATGTAAAA AATAAGCGGG CTTTGCTCGA CGCCTTAGCC ATTGAGATGT    3660

TAGATAGGCA CCATACTCAC TTTTGCCCTT TAGAAGGGGA AAGCTGGCAA GATTTTTTAC    3720

GTAATAACGC TAAAAGTTTT AGATGTGCTT TACTAAGTCA TCGCGATGGA GCAAAAGTAC    3780

ATTTAGGTAC ACGGCCTACA GAAAAACAGT ATGAAACTCT CGAAAATCAA TTAGCCTTTT    3840

TATGCCAACA AGGTTTTTCA CTAGAGAATG CATTATATGC ACTCAGCGCT GTGGGGCATT    3900

TTACTTTAGG TTGCGTATTG GAAGATCAAG AGCATCAAGT CGCTAAAGAA GAAAGGGAAA    3960

CACCTACTAC TGATAGTATG CCGCCATTAT TACGACAAGC TATCGAATTA TTTGATCACC    4020

AAGGTGCAGA GCCAGCCTTC TTATTCGGCC TTGAATTGAT CATATGCGGA TTAGAAAAAC    4080

AACTTAAATG TGAAAGTGGG TCCGCGTACA GCCGCGCGCG TACGAAAAAC AATTACGGGT    4140

CTACCATCGA GGGCCTGCTC GATCTCCCGG ACGACGACGC CCCCGAAGAG GCGGGGCTGG    4200

CGGCTCCGCG CCTGTCCTTT CTCCCCGCGG ACACACGCG CAGACTGTCG ACGGCCCCCC    4260

CGACCGATGT CAGCCTGGGG GACGAGCTCC ACTTAGACGG CGAGGACGTG GCGATGGCGC    4320

ATGCCGACGC GCTAGACGAT TTCGATCTGG ACATGTTGGG GGACGGGGAT TCCCCGGGTC    4380

CGGGATTTAC CCCCCACGAC TCCGCCCCCT ACGCGCTCT GGATATGCC GACTTCGAGT    4440

TTGAGCAGAT GTTTACCGAT GCCCTTGGAA TTGACGAGTA CGGTGGGTAG GGGGCGCGAG    4500
```

```
GATCCTCTAG AGGGCCCTAT TCTATAGTGT CACCTAAATG CTAGAGGATC TTTGTGAAGG    4560

AACCTTACTT CTGTGGTGTG ACATAATTGG ACAAACTACC TACAGAGATT TAAAGCTCTA    4620

AGGTAAATAT AAAATTTTTA AGTGTATAAT GTGTTAAACT ACTGATTCTA ATTGTTTGTG    4680

TATTTTAGAT TCCAACCTAT GGAACTGATG AATGGGAGCA GTGGTGGAAT GCCTTTAATG    4740

AGGAAAACCT GTTTTGCTCA GAAGAAATGC CATCTAGTGA TGATGAGGCT ACTGCTGACT    4800

CTCAACATTC TACTCCTCCA AAAAGAAGA GAAAGGTAGA AGACCCCAAG GACTTTCCTT     4860

CAGAATTGCT AAGTTTTTTG AGTCATGCTG TGTTTAGTAA TAGAACTCTT GCTTGCTTTG    4920

CTATTTACAC CACAAAGGAA AAAGCTGCAC TGCTATACAA GAAAATTATG GAAAATATT     4980

TGATGTATAG TGCCTTGACT AGAGATCATA ATCAGCCATA CCACATTTGT AGAGGTTTTA    5040

CTTGCTTTAA AAAACCTCCC ACACCTCCCC CTGAACCTGA AACATAAAAT GAATGCAATT    5100

GTTGTTGTTA ACTTGTTTAT TGCAGCTTAT AATGGTTACA AATAAAGCAA TAGCATCACA    5160

AATTTCACAA ATAAAGCATT TTTTTCACTG CATTCTAGTT GTGGTTTGTC CAAACTCATC    5220

AATGTATCTT ATCATGTCTG GATCATCCCG CCATGGGTAT ACATCGATGC GGCCGC       5276

(2) INFORMATION FOR SEQ ID NO: 10:

(i) SEQUENCE CHARACTERISTICS:
        (A) LENGTH: 7664 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GGTACCACTA GTAAGCTTAG ATCCACTGTC TGGGATTATA TCAGGACAAC CGAAGCCTGG     60

AAAGTGTATT AGGTAGAGCA TTTTCTTCCA CGTGTTTGGG CACGTTTCCG ACAGCTAGGA    120

TTCCAGCTCT GTCTTTGTAT GTTACAGACT GTAAATCAAT CGCAGGTGAA ACTGTTTGGA    180

CAGTAGGTGG GGATCAAAGA CCCTCCGCCC GTGAGACTCT AGGCGCTTTC CCCTGCCACC    240

AGCCTGTCTC CAGAGATGCT CTGGAAGGAG GCGGGCCCGG GCGGTCTTTC TGCTCTTTAG    300

CGTGGCGGAC GCGGCGGCGG GGGCAGGGCT GGAGCAGAGA GCGCTGCAGT GATAGAACTT    360

TCTGACCCCG CTGCGCAGGG CGGCAGGGTG GCAGGGTGGC AGGGTGGCGA GCTAAGCCAG    420

AGCCGAACGC TGGAGCTCTG GGAGGAACAT CGAAGTGTTT GTATGTGGTC TGAGATCGGC    480

CTGACTATAT TTTTTTGTCC TAAATTTGCA AGCACACACC CACAAAGCTG CGGTCTTGAC    540

CGGTATTCTT TATAGAGCGC AATGGAGTGA GCTGAGTGTC TAAACGATTT CCCTAATTCA    600

TCTGATAGCA GAGGCGCTCT CCTAATTGGC GAAGAGCTGC CTCATGTCCG CAACTTTTTG    660

GCAGAGTGAA TTCCACAGCT TTGTGTGTGT GTGTGGGGG GGGTGTAAGG GGTGTCTAAA    720

ACTTTCGGTC TCCTACTATT CTGTATCTCG ACCGGTTGGT TTTACACCCC GGCTCATCTC    780

ATCAACGCAA ACACCCCCAC TCTCCTATGG ACCCAAGGAC CTGACGTGGG GGAAGGTGGA    840

CATTAGGAAT GTCAGAAACC TAGAGTCCAC GCTCCTCCTC TCCATCTTTC CACGAGTTTG    900

GGAAACTTCT TGGCTGCGAA GACTTTGACC CACATCTGCA TTTCTCAGCC CCAGCTTCCA    960

AAAGTGCTGC AGGTTCGGGA GGGGAGACCT CAGTCCTCCT TTGTGAGGCT TGTTTGCGTT   1020

GAGGGATTGG CAGCGATGGC TTCCAGATGG GCTGAAACCC TGCCCGTATT TATTTAAACT   1080

GGTTCCTCGT GGAGAGCTGT GAATCGGGCT CTGTATGCGC TCGAGAAAAG CCCCATTCAT   1140

GAGAGGCAAG GCCCAGTGGG TCCCCCCGAC TCCCCGACCC CCCTCTCCCA CAATATATCC   1200
```

```
CCCCTCCCTG TGCCCGCCTG CCGCCACCTC CCGGGCTCCG GCCCCGCGCG CAGCGGCGAC   1260
GAAGCAACAC AGTTCCCCGA AAGAGGTAGC TTTTTAATTG GCCAGCCACA AAGAATCACT   1320
TATGCCGCAC GGCGGTAACG AGGGGAACCG GATCGGGCGG CCAGGATGCT ATCTGTGTAG   1380
CCCTTTTCGT GCCACAATTA GGGTGGTGCT GGCTTCCTCC GACCGCACCT AGGCGATCTG   1440
GTTACACTGT TGGCTCCTTT CTTGGGCAGT CATTTAATCC TACTTTTTAC TCTACGAATG   1500
TCTGTCTGAT GGAGGGCTGT GTCCGGAGCC CCATCCACAA AGAGTCAGCC AGCAGCTCTC   1560
ACACCCGGCT GGATCTCATA TGGTGCACTC TCAGTACAAT CTGCTCTGAT GCCGCATAGT   1620
TAAGCCAGCC AAGCTAGCTT GCGCAAGCTA GCTTGCGATC CGTAAAAATG TGTGAGAGTT   1680
ACAAAATGTC TTCCGGGCTA AGATCCGACA GCCATGGTCC AAAGAAGACT TCGGCACTGC   1740
AGACTTAAAA CCAGCTTTCT AGCAGAGGCA GAAGGATCTA GAGCCAAAGG CAAAGACTTG   1800
AATAGGCTGG GAAGATGCAA GAATGGCATT TTACATAAAG AACACTCTCT CCTTTTCCAG   1860
CCAGCACACT TGCATAGAAA TTAAGTTTTA CACTTGAAGT TCTTTGTTTC CATCCTGAGA   1920
AGCTCCAAAG TCTGAGGTGG TGTGGTATGC TGGGTAATTC TCCCCACCCC CCAACATTCC   1980
CTGGGGGTTC CATGGGGGTA GCTTCTCCCA AGGACTTCCA GCGGCAACAC AGAAATCCCA   2040
CTTCGAGACA AAGGAGTTAC TGCTTAAATC AGGCCCTAAT TTCCAAGGTT CCCTTTGCTT   2100
AAAGTTCCCT AGAGGACCAT CTCACTTCTA AAGAAAGGT GTATTCGGGG ACCCATCCTC   2160
AACCTCCTTG TTATGGAAGG AGACTTCGGG AACAGAGCAA GGGCTGAGCC TCCGGCAGTT   2220
TGGGGTAAGG TTGGGGTTGG GGGGAGCAAG GAAGGCAAGT GAGGCTGGAG GCCCAGGGAT   2280
AGGGGAAGAT GTGTGTGTGT GTGTGTGTGT GTGTGTGTGT GTGTGTGTGT CTCGGGGATG   2340
GTGGTGGTGG ACAACTAGGA AACTCTGGCG CTTTCTCCTC CCCTCACAAA ACTGAGTCCA   2400
GCTGGAGCCG CCTCCAGACT CTCTGGCCAG GGCCTCAGAG TGGTCAACAG TCCCTGGCCA   2460
GCGTTGCTCT CTCCAGGCTA AGGGCACCCA CTCCCCTGGA GATTCCTGAA CCTGGGCCAG   2520
GAAGAGCCGA ATTAGACAAG TGTCTCCAAT CCGGCTGCGT GCGGATTTTG TTGCGGTGTC   2580
CCTCGGTTGT CTGCAGTTCC TTTAGTCCCT TCCCTGGCCT GCCCCTTACA CCTCCACACA   2640
GGTCCCCCTC TGTGTAGGAA TACACCAGAC CCTCTCTTAG CCACACACAC CTCCAGTCCC   2700
CCGTCTACCT AGATTTTTTT CATAGCTAGT TGGATGGGGG ATGGGTTAGG GAGGCTGGGT   2760
TTGCGAGCCT CCAGGTGGGA GTTCACCGAC AGGTACTCCG CAAAGGAGCT GGAAGGCAGG   2820
TCTGAAAAAC TGTCCCCCAG ATTTAGGATT CTGGGCAGCT TCCATCAGCT TATACTTTGG   2880
CTCCCCCGCC CCCTAAACTC CCCATCCCCA CCTTCCTTTC TCCCGTTACT TCGTCCTCCC   2940
TCGCCTTTCC AGCCTTGAGT CTAAAGCTCC ATGCTTATGC CTCTGCAAAC AACCCCCTCC   3000
CTTCTAACCC CAGCAGAACT CCGAGGAAAG GGGCCGGAGG CCCCCCTTCT CGCCTGTGGT   3060
TAGAGGGGGC AGTGTGGCAG TCCCAAGTGG GGGCGACCGG AGGCCGTCTC GGTGCCCCGC   3120
CCGATCAGGC CACTGGGCAC ATCGGGGCG GGAAGCTGGG CTCACCAAAG GGCGACTGG    3180
CCTTGGCAGG TGTGGGCTCT GGTCCGGCCT GGGCAGGCTC CGGGGCGGG GTCTCAGGTT   3240
ACAGCCCCGC GGGGGGCTGG GGGCGGCC GCGGTTTGGG CTGGTTTGCC AGCCTTTGGA    3300
GCGACCGGGA GCATATAACC GGAGCCTCTG CTGGGAGAAG ACGCAGAGCG CCGCTGGGCT   3360
GCCGGGTCTC CTGCCTCCTC CTCCTGCTCC TAGAGCCTCC TGCATGAGGG CGCGGTAGAG   3420
ACCCGGACCC GCTCCGTGCT CTGCCGCCTC GCCGAGCTTC GCCCGCAAGC TGGGGAATTC   3480
GGATCCCCGG GATCGAAAGA GCCTGCTAAA GCAAAAAAGA AGTCACCATG TCGTTTACTT   3540
TGACCAACAA GAACGTGATT TTCGTTGCCG GTCTGGGAGG CATTGGTCTG GACACCAGCA   3600
```

```
AGGAGCTGCT CAAGCGCGAT CCCGTCGTTT TACAACGTCG TGACTGGGAA AACCCTGGCG    3660

TTACCCAACT TAATCGCCTT GCAGCACATC CCCCTTTCGC CAGCTGGCTT TATAGCGAAG    3720

AGGCCCGCAC CGATCGCCCT TCCCAACAGT TGCGCAGCCT GAATGGCGAA TGGCGCTTTG    3780

CCTGGTTTCC GGCACCAGAA GCGGTGCCGG AAAGCTGGCT GGAGTGCGAT CTTCCTGAGG    3840

CCGATACTGT CGTCGTCCCC TCAAACTGGC AGATGCACGG TTACGATGCG CCCATCTACA    3900

CCAACGTAAC CTATTCCATT ACGGTCAATC CGCCGTTTGT TCCCACGGAG AATCCGACGG    3960

GTTGTTACTC GCTCACATTT AATGTTGATG AAAGCTGGCT ACAGGAAGGC CAGACGCGAA    4020

TTATTTTTGA TGGCGTTAAC TTGGCGTTTC ATCTGTGGTG CAACGTGCGC TGGGTCGGTT    4080

ACGGCCAGGA CAGTCGTTTG CCGTCTGAAT TTGACCTGAG CGCATTTTTA CGCGCCGGAG    4140

AAAACCGCCT CGCGGTGATG GTGCTGCGTT GGAGTGACGG CAGTTATCTG GAAGATCAGG    4200

ATATGTGGCG GATGAGCGGC ATTTTCCGTG ACGTCTCGTT GCTGCATAAA CCGACTACAC    4260

AAATCAGCGA TTTCCATGTT GCCACTCGCT TTAATGATGA TTTCAGCCGC GCTGAACTGG    4320

AGGCTGAAGT TCAGATGTGC GGCGAGTTGC GTGACTACCT ACGGGTAACA GTTTCTTTAT    4380

GGCAGGGTGA AACGCAGGTC GCCAGCGGCA CCGCGCCTTT CGGCGGTGAA ATTATCGATG    4440

AGCGTGGTGG TTATGCCGAT CGCGTCACAC TACGTCTGAA CGTCGAAAAC CCGAAACTGT    4500

GGAGCGCCGA AATCCCGAAT CTCTATCGTG CGGTGGTTGA ACTGCACACC GCCGACGGCA    4560

CGCTGATTGA AGCAGAAGCC TGCGATGTCG GTTTCCGCGA GGTGCGGATT GAAAATGGTC    4620

TGCTGCTGCT GAACGGCAAG CCGTTGCTGA TTCGAGGCGT TAACCGTCAC GAGCATCATC    4680

CTCTGCATGG TCAGGTCATG GATGAGCAGA CGATGGTGCA GGATATCCTG CTGATGAAGC    4740

AGAACAACTT TAACGCCGTG CGCTGTTCGC ATTATCCGAA CCATCCGCTG TGGTACACGC    4800

TGTGCGACCG CTACGCCTG TATGTGGTGG ATGAAGCCAA TATTGAAACC CACGGCATGG    4860

TGCCAATGAA TCTGCTGACC GATGATCCGC GCTGGCTACC GGCGATGAGC GAACGCGTAA    4920

CGCGAATGGT GCAGCGCGAT CGTAATCACC CGAGTGTGAT CATCTGGTCG CTGGGGAATG    4980

AATCAGGCCA CGGCGCTAAT CACGACGCGC TGTATCGCTG GATCAAATCT GTCGATCCTT    5040

CCCGCCCGGT GCAGTATGAA GGCGGCGGAG CCGACACCAC GGCCACCGAT ATTATTTGCC    5100

CGATGTACGC GCGCGTGGAT GAAGACCAGC CCTTCCCGGC TGTGCCGAAA TGGTCCATCA    5160

AAAAATGGCT TTCGCTACCT GGAGAGACGC GCCCGCTGAT CCTTTGCGAA TACGCCCACG    5220

CGATGGGTAA CAGTCTTGGC GGTTTCGCTA AATACTGGCA GGCGTTTCGT CAGTATCCCC    5280

GTTTACAGGG CGGCTTCGTC TGGGACTGGG TGGATCAGTC GCTGATTAAA TATGATGAAA    5340

ACGGCAACCC GTGGTCGGCT TACGGCGGTG ATTTTGGCGA TACGCCGAAC CATCGCCAGT    5400

TCTGTATGAA CGGTCTGGTC TTTGCCGACC GCACGCCGCA TCCAGCGCTG ACGGAAGCAA    5460

AACACCAGCA GCAGTTTTTC CAGTTCCGTT TATCCGGGCA AACCATCGAA GTGACCAGCG    5520

AATACCTGTT CCGTCATAGC GATAACGAGC TCCTGCACTG GATGGTGGCG CTGGATGGTA    5580

AGCCGCTGGC AAGCGGTGAA GTGCCTCTGG ATGTCGCTCC ACAAGGTAAA CAGTTGATTG    5640

AACTGCCTGA ACTACCGCAG CCGGAGAGCG CCGGGCAACT CTGGCTCACA GTACGCGTAG    5700

TGCAACCGAA CGCGACCGGA TGGTCAGAAG CCGGGCACAT CAGCGCCTGG CAGCAGTGGC    5760

GTCTGGCGGA AAACCTCAGT GTGACGCTCC CCGCCGCGTC CCACGCCATC CCGCATCTGA    5820

CCACCAGCGA AATGGATTTT TGCATCGAGC TGGGTAATAA GCGTTGGCAA TTTAACCGCC    5880

AGTCAGGCTT TCTTTCACAG CTGTGGATTG GCGATAAAAA ACAACTGCTG ACGCCGCTGC    5940
```

```
GCGATCAGTT CACCCGTGCA CCGCTGGATA ACGACATTGG CGTAAGTGAA GCGACCCGCA        6000

TTGACCCTAA CGCCTGGGTC GAACGCTGGA AGGCGGCGGG CCATTACCAG GCCGAAGCAG        6060

CGTTGTTGCA GTGCACGGCA GATACACTTG CTGATGCGGT GCTGATTACG ACCGCTCACG        6120

CGTGGCAGCA TCAGGGGAAA ACCTTATTTA TCAGCCGGAA AACCTACCGG ATTGATGGTA        6180

GTGGTCAAAT GGCGATTACC GTTGATGTTG AAGTGGCGAG CGATACACCG CATCCGGCGC        6240

GGATTGGCCT GAACTGCCAG CTGGCGCAGG TAGCAGAGCG GGTAAACTGG CTCGGATTAG        6300

GGCCGCAAGA AAACTATCCC GACCGCCTTA CTGCCGCCTG TTTTGACCGC TGGGATCTGC        6360

CATTGTCAGA CATGTATACC CCGTACGTCT TCCCGAGCGA AAACGGTCTG CGCTGCGGGA        6420

CGCGCGAATT GAATTATGGC CCACACCAGT GGCGCGGCGA CTTCCAGTTC AACATCAGCC        6480

GCTACAGTCA ACAGCAACTG ATGGAAACCA GCCATCGCCA TCTGCTGCAC GCGGAAGAAG        6540

GCACATGGCT GAATATCGAC GGTTTCCATA TGGGGATTGG TGGCGACGAC TCCTGGAGCC        6600

CGTCAGTATC GGCGGAATTA CAGCTGAGCG CCGGTCGCTA CCATTACCAG TTGGTCTGGT        6660

GTCAAAAATA ATAATAACCG GCAGGCCATG TCTGAAAGTA TTCGCGTAAG GAAATCCATT        6720

ATGTACTATT TAAAAACAC AAACTTTTGG ATGTTCGGTT TATTCTTTTT CTTTTACTTT         6780

TTTATCATGG GAGCCTACTT CCCGTTTTTC CCGATTTGGC TACATGACAT CAACCATATG        6840

AGCAAAAGTG ATACGGGTAT TATTTTTGCC GCTATTTCTC TGTTGTCGCT ATTATTCCAA        6900

CCGCTGTTGG TCTGCTTTCT GACAAACTCG GCCTCGACTC TAGACTGAGA ACTTCAGGGT        6960

GAGTTTGGGG ACCCTTGATT GTTCTTTCTT TTTCGCTATT GAAAAATTCA TGTTATATGG        7020

AGGGGGCAAA GTTTTCAGGG TGTTGTTTAG AATGGGAAGA TGTCCCTTGT ATCACCATGG        7080

ACCCTCATGA TAATTTTGTT TCTTTCACTT TCTACTCTGT TGACAACCAT TGTCTCCTCT        7140

TATTTTCTTT TCATTTTCTG TAACTTTTTT CGTTAAACTT TAGCTTGCAT TTGTAACGAA        7200

TTTTTAAATT CACTTTCGTT TATTTGTCAG ATTGTAAGTA CTTTCTCTAA TCACTTTTTT        7260

TTCAAGGCAA TCAGGGTAAT TATATTGTAC TTCAGCACAG TTTTAGAGAA CAATTGTTAT        7320

AATTAAATGA TAAGGTAGAA TATTTCTGCA TATAAATTCT GGCTGGCGTG GAAATATTCT        7380

TATTGGTAGA AACAACTACA TCCTGGTAAT CATCCTGCCT TTCTCTTTAT GGTTACAATG        7440

ATATACACTG TTTGAGATGA GGATAAAATA CTCTGAGTCC AAACCGGGCC CCTCTGCTAA        7500

CCATGTTCAT GCCTTCTTCT TTTTCCTACA GCTCCTGGGC AACGTGCTGG TTGTTGTGCT        7560

GTCTCATCAT TTTGGCAAAG AATTCACTCC TCAGGTGCAG GCTGCCTATC AGAAGGTGGT        7620

GGCTGGTGTG GCCAATGCCC TGGCTCACAA ATACCACTGA GATC                        7664
```

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 11:

```
CGAGGGCCTG CTCGATCTCC                                                     20
```

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

GGCATTCCAC CACTGCTCCC                                                 20

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 13:

GAGCACCCTT CTCATGACCT C                                               21

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 14:

GTTGGTGTAG ATGGGCGCAT CG                                              22

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 15:

GCGGGGTCTC AGGTTACAGC C                                               21

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 16:

GCCCTCTGGC CTGCTGGCTC ATG                                             23

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

CAGGAGAGTC TTGCCTGTAT CCTC                                            24

(2) INFORMATION FOR SEQ ID NO: 18:

(i) SEQUENCE CHARACTERISTICS:
        (A) LENGTH: 1521 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 18:

```
CAAGATGCAT CCAGGGGTCC TGGCTGCCTT CCTCTTCTTG AGCTGGACTC ATTGTCGGGC    60

CCTGCCCCTT CCCAGTGGTG GTGATGAAGA TGATTTGTCT GAGGAAGACC TCCAGTTTGC   120

AGAGCGCTAC CTGAGATCAT ACTACCATCC TACAAATCTC GCGGGAATCC TGAAGGAGAA   180

TGCAGCAAGC TCCATGACTG AGAGGCTCCG AGAAATGCAG TCTTTCTTCG GCTTAGAGGT   240

GACTGGCAAA CTTGACGATA ACACCTTAGA TGTCATGAAA AAGCCAAGAT GCGGGGTTGT   300

CGATGTGGG TGAATACAATG TTTTCCCTCG AACTCTTAAA TGGTCCAAAA TGAATTTAAC   360

CTACAGAATT GTGAATTACA CCCCTGATAT GACTCATTCT GAAGTCGAAA AGGCATTCAA   420

AAAAGCCTTC AAAGTTTGGT CCGATGTAAC TCCTCTGAAT TTTACCAGAC TTCACGATGG   480

CATTGCTGAC ATCATGATCT CTTTTGGAAT TAAGGAGCAT GGCGACTTCT ACCCATTTGA   540

TGGGCCCTCT GGCCTGCTGG CTCATGCTTT TCCTCCTGGG CCAAATTATG GAGGAGATGC   600

CCATTTTGAT GATGATGAAA CCTGGACAAG TAGTTCCAAA GGCTACAACT TGTTTCTTGT   660

TGCTGCGCAT GAGTTCGGCC ACTCCTTAGG TCTTGACCAC TCCAAGGACC TGGAGCACT   720

CATGTTTCCT ATCTACACCT ACACCGGCAA AAGCCACTTT ATGCTTCCTG ATGACGATGT   780

ACAAGGGATC CAGTCTCTCT ATGGTCCAGG AGATGAAGAC CCCAACCCTA ACATCCAAA   840

AACGCCAGAC AAATGTGACC CTTCCTTATC CCTTGATGCC ATTACCAGTC TCCGAGGAGA   900

AACAATGATC TTTAAAGACA GATTCTTCTG GCGCCTGCAT CCTCAGCAGG TTGATGCGGA   960

GCTGTTTTTA ACGAAATCAT TTTGGCCAGA ACTTCCCAAC CGTATTGATG CTGCATATGA  1020

GCACCCTTCT CATGACCTCA TCTTCATCTT CAGAGGTAGA AAATTTTGGG CTCTTAATGG  1080

TTATGACATT CTGGAAGGTT ATCCCAAAAA AATATCTGAA CTGGGTCTTC CAAAAGAAGT  1140

TAAGAAGATA AGTGCAGCTG TTCACTTTGA GGATACAGGC AAGACTCTCC TGTTCTCAGG  1200

AAACCAGGTC TGGAGATATG ATGATACTAA CCATATTATG GATAAAGACT ATCCGAGACT  1260

AATAGAAGAA GACTTCCCAG GAATTGGTGA TAAAGTAGAT GCTGTCTATG AGAAAAATGG  1320

TTATATCTAT TTTTTCAACG GACCCATACA GTTTGAATAC AGCATCTGGA GTAACCGTAT  1380

TGTTCGCGTC ATGCCAGCAA ATTCCATTTT GTGGTGTTAA GTGTCTTTTT AAAAATTGTT  1440

ATTTAAATCC TGAAGAGCAT TTGGGGTAAT ACTTCCAGAA GTGCGGGGTA GGGGAAGAAG  1500

AGCTATCAGG AGAAAGCTTG G                                           1521
```

(2) INFORMATION FOR SEQ ID NO: 19

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

```
Pro Arg Cys Gly Xaa Pro Asp
 1               5
```

(2) INFORMATION FOR SEQ ID NO: 20:

(i) SEQUENCE CHARACTERISTICS:
        (A) LENGTH: 12 amino acids

```
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 20:

His Glu Xaa Gly His Xaa Xaa Xaa Xaa Xaa His Ser
 1               5                  10

(2) INFORMATION FOR SEQ ID NO: 21:

(i) SEQUENCE CHARACTERISTICS:
            (A) LENGTH: 471 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 21:

Met His Pro Gly Val Leu Ala Ala Phe Leu Phe Leu Ser Trp Thr His
 1               5                  10                  15

Cys Arg Ala Leu Pro Leu Pro Ser Gly Gly Asp Glu Asp Asp Leu Ser
                20                  25                  30

Glu Glu Asp Leu Gln Phe Ala Glu Arg Tyr Leu Arg Ser Tyr Tyr His
            35                  40                  45

Pro Thr Asn Leu Ala Gly Ile Leu Lys Glu Asn Ala Ala Ser Ser Met
        50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Asp Val Gly Glu Tyr Asn Val Phe Pro Arg Thr Leu Lys
                100                 105                 110

Trp Ser Lys Met Asn Leu Thr Tyr Arg Ile Val Asn Tyr Thr Pro Asp
            115                 120                 125

Met Thr His Ser Glu Val Glu Lys Ala Phe Lys Lys Ala Phe Lys Val
        130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
        195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
        275                 280                 285

Ser Leu Asp Ala Ile Thr Ser Leu Arg Gly Glu Thr Met Ile Phe Lys
```

-continued

```
            290                 295                 300
Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
                340                 345                 350

Lys Phe Trp Ala Leu Asn Gly Tyr Asp Ile Leu Glu Gly Tyr Pro Lys
                355                 360                 365

Lys Ile Ser Glu Leu Gly Leu Pro Lys Glu Val Lys Lys Ile Ser Ala
    370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
                420                 425                 430

Ala Val Tyr Glu Lys Asn Gly Tyr Ile Tyr Phe Phe Asn Gly Pro Ile
                435                 440                 445

Gln Phe Glu Tyr Ser Ile Trp Ser Asn Arg Ile Val Arg Val Met Pro
    450                 455                 460

Ala Asn Ser Ile Leu Trp Cys
465                 470
```

TRANSGENIC ANIMAL MODEL FOR DEGENERATIVE DISEASES OF CARTILAGE

This is a continuation of application Ser. No. 08/994,689, filed Dec. 19, 1997 now U.S. Pat. No. 6,613,958. Each prior application is hereby incorporated herein by reference, in its entirety.

FIELD OF THE INVENTION

The present invention pertains to transgenic mammals that express recombinant matrix-degrading enzymes in a temporally and spatially regulated manner. The invention further pertains to model systems incorporating such transgenic mammals for studying degenerative joint diseases, including systems for identifying therapeutic agents and treatment regimens.

BACKGROUND OF THE INVENTION

Degenerative diseases of cartilage, including joint and disc diseases such as osteoarthritis, rheumatoid arthritis, and osteochondrodysplasias, are widespread, particularly in the elderly. Early symptoms common to these diseases include progressive loss of proteoglycans in the joint (as evidenced by loss of metachromasia); collagen degradation; fibrillation of the cartilage surface; and, ultimately, loss of cartilage (which is evidenced radiologically as joint space narrowing).

One of the primary targets affected by these diseases is type II collagen, the major structural collagen found in articular cartilage. There is a balance between the production of type II collagen and catabolic enzymes that degrade type II collagen during normal remodeling of cartilage and bone. Pathological conditions such as, e.g., degenerative joint diseases, may result when this balance is disrupted.

Among the enzymes that degrade extracellular matrix components are matrix metalloproteinases (MMPs), a family of zinc-dependent enzymes, and aggrecanase (Table 1).

TABLE 1

Matrix-Degrading Enzymes

| | \multicolumn{7}{c}{SUBSTRATES} |
|---|---|---|---|---|---|---|---|
| | Collagen | Gelatin | Proteoglycan | Fibronectin | Laminin | Elastin | Other |
| I. Metalloproteinases Collagenases | | | | | | | |
| MMP-1 (intestinal collagenase) | I, II, III VII, X | ✓ | | | | | |
| MMP-8 (neutrophil collagenase) | I, II, III | | | | | | |
| MMP-13 (collagenase 3) | I, II, III | ✓ | | | | | |
| Gelatinases | | | | | | | |
| MMP-2 (gelatinase A) | IV, V, VII, XI | ✓ | | ✓ | ✓ | ✓ | |
| MMP-9 (gelatinase B) | IV, V | ✓ | ✓ | | | | |
| Stromelysins | | | | | | | |
| MMP-3 (stromelysin 1) | | ✓ | ✓ | ✓ | ✓ | | activates MMP zymogens |
| MMP-7 (matrilysin) | IV | ✓ | ✓ | ✓ | ✓ | ✓ | |
| MMP-10 (stromelysin 2) | IV, V, IX | | ✓ | ✓ | ✓ | | activates MMP zymogens |
| MMP-11 (stromelysin 3) | IV | | | ✓ | ✓ | | activates serpins |
| Other | | | | | | | |
| MMP-12 (metalloelastase) | | | | | | ✓ | |
| MMP-14 | | ✓ | | | | | proMMP-2, proMMP-13 |
| MMP-15 | | | | | | | |
| MMP-16 | | | | | | | proMMP-2 |
| MMP-17 | | | | | | | |
| II. Aggrecanase | | | ✓ | | | | |

MMPs are synthesized in articulating joints by chondrocytes, which, in mature articular cartilage, are terminally differentiated cells that maintain the cartilage-specific matrix phenotype. Overexpression of MMPs relative to endogenous MMP inhibitors, as occurs in degenerative joint diseases, may result in cartilage degradation. For example, Type II collagen is a substrate for MMP-13 and MMP-1 (Knauper et al., *J. Biol. Chem.* 271:1544, 1996) and both MMP-1 and MMP-13 proteins can be detected immunohistochemically in human osteoarthritic tissues. In some cases, MMP-13 and its cleavage products are found at higher levels than MMP-1. Billinghurst et al., *J. Clin. Inves.* 99:1534, 1997. Thus, MMP-13 may play an important role in cartilage degradation associated with osteoarthritis and other degenerative joint diseases. (Mitchell et al., *J. Clin. Inves.* 97:761, 1996).

Animal models for osteoarthritis-related syndromes have been described in guinea pigs (Watson et al., *Arth. Rheum.* 3: 1327, 1996) and in the inbred STR/ORT strain of mice (Das-Gupta et al., *Int. J. Exp. Path.* 74:627, 1993). In guinea pigs, spontaneous osteoarthritis has a long course of development (six months or more), and only certain sublines of STR/ORT mice consistently develop degenerative joint disease. Thus, the duration and/or variability of these models renders them less applicable to drug discovery studies.

Other osteoarthritis-related models include surgically-induced joint destabilization, e.g., anterior cruciate ligament transection and/or partial meniscectomy in rabbits and dogs, which stimulates cartilage degradation. Hulth et al., *Acta Orthop. Scand.* 41:522, 1970. Another model employs injection of bacterial collagenase into the joints of an animal to induce a biochemical ligament transection. Van der Kraan et al., *J. Exp. Pathol.* 71:19, 1990. Because (i) surgical or other manipulation of individual animals is required; (ii) the animals are large and expensive; and/or (iii) the course of disease is not consistent, these models cannot easily be used in large-scale studies, including drug screening.

Transgenic animal models, in principle, can provide the opportunity for a reproducible animal model system for degenerative joint diseases. However, previous attempts to engineer transgenic animals expressing MMPs such as MMP-1 and stromelysin have not resulted in an observable joint degeneration phenotype in the transgenic animals. This could be due to embryonic lethality caused by constitutive expression of these enzymes. Witty et al., *Mol. Biol. Cell* 6:1287, 1995, have created transgenic animals that constitutively express MMP-1 and stromelysin in mammary tissue, but these animals do not exhibit symptoms of osteoarthritis. D'Armiento et al., *Cell* 71:955, 1992, disclose transgenic mice that express human interstitial collagenase in the lung. Liu et al., *J. Cell Biol.* 130:227, 1995, disclose transgenic animals that overexpress mutated type II collagen, resulting in connective tissue defects but not osteoarthritis. None of these transgenic animal systems provides a useful animal model for osteoarthritis. Khokha et al., *Cancer and Metastasis Rev.* 14:97, 1995; Shapiro, *Matrix Biol.* 15:527, 1997.

Thus, there is a need in the art for animal model systems that mimic human degenerative joint diseases such as, e.g., osteoarthritis, rheumatoid arthritis, and chondrodysplasias. Transgenic animals containing regulatable heterologous genes whose expression results in cartilage degeneration are particularly advantageous in providing reproducible experimental control over the timing and the level of expression of the transgenes and, thereby, over the pathological syndrome itself. Such animals can be used to determine what level of expression of the transgene is required to cause disease and, importantly, can be used for drug discovery and optimization of treatment regimens. In particular, such transgenic animals can be used to further define the role of matrix-degrading enzymes in cartilage degradation and as an in vivo screen to identify compounds that modulate these enzymes or compounds that inhibit the progression of degenerative joint diseases.

SUMMARY OF THE INVENTION

The present invention provides transgenic non-human animals or the progeny thereof whose somatic and germline cells contain, in stably integrated form, one or more heterologous or recombinant genes encoding polypeptides comprising enzymatically active matrix-degrading enzymes (MDEs), preferably MMPs. MMPs for use in the invention comprise one or more of MMP-1, MMP-2, MMP-3, MMP-7, MMP-8, MMP-9, MMP-10, MMP-11, MMP-12, MMP-13, MMP-14, MMP-15, MMP-16, and MMP-17; preferably one or more of MMP-1, MMP-3, MMP-8, and MMP-13; and most preferably one or more of MMP-1 and MMP-13; and include enzymatically active variants, fragments, and combinations of these polypeptides. Other matrix-degrading enzymes can also be used, including, e.g., aggrecanase. The MDEs may be derived from any species, preferably human. In preferred embodiments, the recombinant MDE-encoding genes are selectively expressed in articular chondrocytes of the transgenic animal and expression results in pathological symptoms characteristic of degenerative joint disease.

In one aspect, the invention provides a transgenic animal or the progeny thereof whose somatic and germline cells contain a stably integrated first recombinant gene encoding an MDE or an enzymatically active derivative or variant thereof, preferably a constitutively active proMMP-13 variant (designated MMP-13*) comprising the sequence depicted in SEQ ID NO: 1. Preferably, the first recombinant gene is under the control of a first regulatable promoter; most preferably, the first regulatable promoter comprises a tet07 sequence, such as, e.g., the promoter depicted in SEQ ID NO: 2. The transgenic animal may further comprise a second recombinant gene encoding a polypeptide that regulates the first regulatable promoter and is preferably a tTA polypeptide. In these embodiments, the second recombinant gene is under the control of a second regulatable promoter, preferably one that comprises sequences derived from a joint-specific promoter, and most preferably a type II collagen promoter, such as, e.g., the promoter depicted in SEQ ID NO: 3. Selective expression of the second recombinant gene in joint tissues thus results in regulated joint-specific expression of the recombinant MDE.

In another aspect, the invention provides isolated nucleic acids encoding enzymatically active MMP variants, preferably human proMMP-13 variants, and most preferably MMP-13*. The invention also encompasses recombinant cloning vectors comprising these nucleic acids; cells comprising the vectors; methods for producing MMP-13-derived polypeptides comprising culturing the cells under conditions appropriate for MMP-13 expression; and isolated MMP-13-derived polypeptides.

In yet another aspect, the invention provides methods for producing phenotypic changes characteristic of cartilage-degenerative disease in a mammal, which comprise exposing the transgenic animals of the invention to conditions that result in expression of the MDEs encoded by the transgenes. In a preferred embodiment, a transgenic animal comprising a first recombinant gene encoding MMP-13* operably linked to a tet07 promoter and a second recombinant gene encoding a tTA protein operably linked to a type II collagen promoter is maintained in the presence of tetracycline or a tetracycline analogue. When it is desired to induce expression of MMP-13*, tetracycline or the tetracycline analogue is withdrawn, MMP-13* is selectively expressed in joint tissues, and phenotypic changes characteristic of cartilage-degenerative disease result.

In yet another aspect, the invention provides methods for determining the potential of a composition to counteract cartilage-degenerative disease. The methods are carried out by administering a known dose of the composition to the transgenic animals of the invention, either before or after phenotypic indicators of cartilage-degenerative disease have developed; monitoring the indicators for a predetermined time following administration of the composition; and comparing the extent of the indicators in the animal to which the composition was administered relative to a control transgenic animal that had not been exposed to the composition. Any difference in (i) the nature or extent of phenotypic indicators of cartilage-degenerative disease, (ii) the time required for the indicators to develop, or (iii) the need for other ameliorative treatments indicates the potential of the composition to counteract cartilage-degenerative disease.

BRIEF DESCRIPTION OF THE DRAWINGS

FIG. 2A shows a nucleic acid construct comprising, in a 5' to 3' direction: (i) sequences derived from rat type II collagen promoter; (ii) sequences encoding a tetracycline repressor polypeptide fused in frame to sequences encoding a VP16 transcriptional activator polypeptide; and (iii) sequences comprising an SV40-derived RNA splice site and polyadenylation signal. FIG. 2B shows a nucleic acid construct comprising, in a 5' to 3' direction: (i) sequences derived from a bacterial tet07 promoter; (ii) sequences encoding human MMP-13*; and (iii) sequences comprising an SV40-derived RNA splice site and polyadenylation signal.

DETAILED DESCRIPTION OF THE INVENTION

Figure 1:
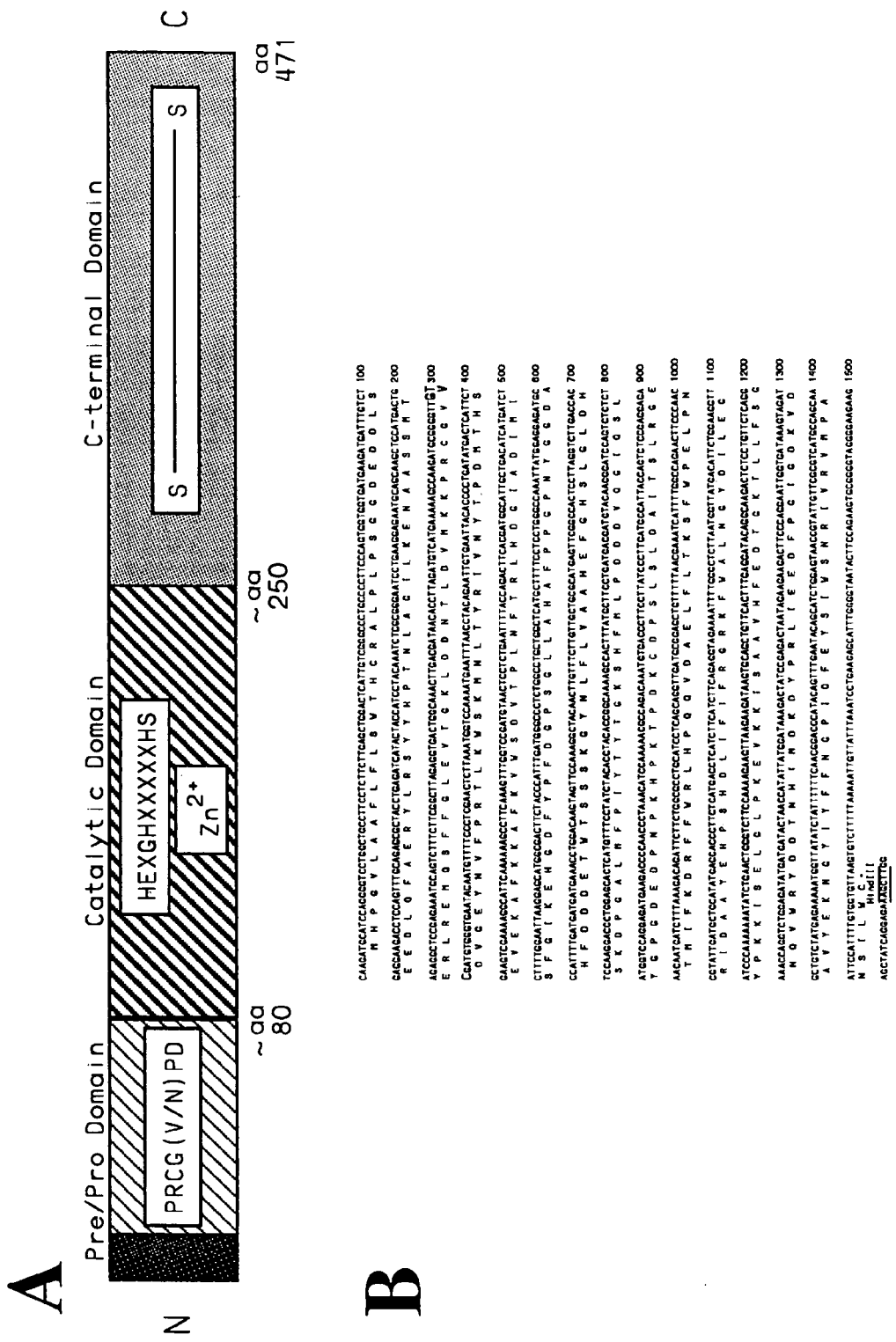
FIG. 1A is a schematic illustration of the structure of human MMP-13 (collagenase-3). The black box at the extreme aminoterminus represents the pre domain (signal peptide) that targets nascent proMMP-13 for secretion. The lightly hatched box represents the pro domain SEQ ID NO: 19, which is involved in maintaining the latency of the enzyme. A conserved sequence within the pro domain that is important for maintaining enzyme latency is shown. The heavily hatched box represents the 170-amino acid catalytic domain SEQ ID NO: 20, which contains a conserved region (shown) that is important for catalytic activity. The shaded box represents the 200-amino acid carboxyterminal domain.
FIG. 1B is an illustration of the nucleic acid sequence encoding a constitutively active variant of human pro MMP-13 SEQ ID NO: 18, designated MMP-13*, and the amino acid sequence of MMP-13*, SEQ ID NO: 1. The residues that are mutated relative to wild-type MMP-13, which are depicted in larger type, are GTC at nucleotide positions 299–301.

The present inventors have discovered that regulated expression of matrix-degrading enzymes in cartilage in transgenic mice results in characteristic phenotypic changes associated with matrix degenerative diseases of the joints and intervertebral discs. The animal models of the invention provide novel model systems for matrix degenerative disease syndromes which can be used for detailed characterization of human joint and intervertebral disc pathologies as well as for drug discovery and optimization of treatment regimens.

A transgenic animal according to the invention is an animal having cells that contain a transgene which was introduced into the animal or an ancestor of the animal at a prenatal (embryonic) stage. A transgenic animal can be created, for example, by introducing the gene of interest into the male pronucleus of a fertilized oocyte by, e.g., microinjection, and allowing the oocyte to develop in a pseudopregnant female foster animal. The gene of interest may include appropriate promoter sequences, as well as intronic sequences and polyadenylation signal sequences. Methods for producing transgenic animals are disclosed in, e.g., U.S. Pat. Nos. 4,736,866 and 4,870,009 and Hogan et al., *A Laboratory Manual*, Cold Spring Harbor Laboratory, 1986. A transgenic founder animal can be used to breed additional animals carrying the transgene. A transgenic animal carrying one transgene can also be bred to another transgenic animal carrying a second transgene to create a "double transgenic" animal carrying two transgenes. Alternatively, two transgenes can be co-microinjected to produce a double transgenic animal. Animals carrying more than two transgenes are also possible. Furthermore, heterozygous transgenic animals, i.e., animals carrying one copy of a transgene, can be bred to a second animal heterozygous for the same transgene to produce homozygous animals carrying two copies of the transgene.

The present invention encompasses transgenic animals, preferably mammals, which express MDEs, particularly MMPs, and most particularly those MMPs having collagenase activity, from a recombinant gene. MDEs for use in the invention include without limitation MMPs and aggrecanase. Useful MMPs include without limitation the collagenases designated MMP-1, MMP-8 and MMP-13; the stromelysins designated MMP-3, MMP-10, and MMP-11; the gelatinases designated MMP-2 and MMP-9; the metalloelastase designated MMP-12; and membrane-type MMPs designated MMP-14, MMP-15, MMP-16, and MMP-17. Matrisian, *BioEssays*, 14:455, 1992. Matrix-degrading activity as used herein refers to the proteolytic degradation of matrix components, including, e.g., collagen, particularly type II collagen and most particularly the triple helical form of type II collagen. Any polypeptide exhibiting matrix-degrading activity may be used in practicing the invention, including enzymatically active fragments of the above-described enzymes. Preferably, MMP-13 enzymatic activity is expressed. MMP-13 enzymatic activity as used herein refers to the proteolytic degradation of type II collagen. Any MMP-13 polypeptide or fragment or derivative thereof that exhibits MMP-13 enzymatic activity may be used. The enzymes may be derived from any animal species, including without limitation human, mouse, rat, rabbit, pig, cow, or non-human primate, or combinations thereof. Preferably, the MMP-13 or derivative thereof is of human origin.

Normally, MMPs are synthesized as precursors (i.e., zymogens or proenzymes) whose enzymatic activity is latent; proteolytic removal of the pro region after secretion produces the enzymatically active protein. In preferred embodiments of the invention, the need for proteolytic processing is circumvented by the use of enzyme or proenzyme variants that are enzymatically active even when uncleaved. Such variants can be produced using conventional techniques for site-directed or random mutagenesis coupled with analysis of collagenase enzymatic activity (see below). In this manner, modifications (including, e.g., insertions, deletions, and substitutions), may be introduced into a proenzyme sequence, particularly within the pro region or near the pro region cleavage site, to produce a constitutively active polypeptide which does not require proteolytic processing for activation. Alternatively, the pro region may be deleted entirely. Furthermore, recombinant genes may be used in which the sequence encoding the native signal peptide is replaced by a heterologous sequence that functions as a signal peptide, i.e., promotes secretion. The use of genes encoding any such modified MMP polypeptides is encompassed by the invention.

Preferably, a constitutively active MMP-13 variant is used in practicing the invention. Most preferably, the MMP-13 variant comprises a sequence containing a mutation in the sequence encoding the PRCGVPDV region, SEQ ID NO:4, specifically a substitution of $Pro^{99}$ to Val; the sequence of this polypeptide is depicted in SEQ ID NO: 1 and this polypeptide is designated MMP-13*. In another embodiment, the constitutively active MMP-13 variant comprises a substitution of $Val^{98}$ to Gly SEQ ID NO. 21.

The transgenic animals of the invention preferably express MMP activity in a regulated manner. Regulated expression as used herein refers to temporal and/or spatial control. Temporal control refers to the ability to repress expression of MMP activity until a predetermined time in the development of the transgenic animal, after which MMP expression may be activated and maintained for as long as desired. Preferably, MMP expression is repressed throughout embryonic development and activated in the adult animal. Spatial control refers to the ability to selectively express MMP activity in particular tissues. Preferably, MMP activity is selectively expressed in joint tissues, most preferably in articular chondrocytes.

Temporal control of MMP expression is achieved by use of one or more polypeptides comprising a transcriptional repressor, a transcriptional activator or enhancer, or combinations thereof, in conjunction with a promoter responsive to the transcriptional repressor/activator used to which the MMP-encoding sequence is operably linked. In one set of embodiments, temporal control of MMP expression is achieved by (i) expression in the transgenic animal of a repressor polypeptide operably linked to a polypeptide that directly or indirectly activates transcription in eucaryotic cells, creating a repressor-activator fusion polypeptide; and (ii) the coupled use of a target promoter operably linked to an MMP-encoding sequence whose transcriptional activity is responsive to the repressor-activator fusion polypeptide. Typically, nucleotide sequences encoding the repressor polypeptide are ligated in-frame to sequences encoding the transcriptional activator polypeptide to create a chimeric gene encoding a fusion protein.

Useful repressor polypeptides include without limitation polypeptides comprising sequences derived from bacterial repressors, including without limitation tetracycline repressor, LacR repressor, KRAB domain, and lambda repressor (cro and cI), as well as eukaryotic repressors, including without limitation those involved in amino acid or sugar synthesis. Useful direct transcriptional activator polypeptides include without limitation herpes simplex virus protein 16 (VP16); yeast GAL14; yeast STAT; steroid receptors such as, e.g., progesterone receptor and estrogen receptor; and constitutive activators such as, e.g., c-fos, c-jun, and SP-1. Alternatively, the repressor polypeptide may be linked to a polypeptide that indirectly activates transcription by recruiting a transcriptional activator to interact with the repressor-activator fusion protein; such indirect activator polypeptides include without limitation TATA Box Binding Protein (TBP) and basic transcription factors, including, e.g., basic transcription factor D.

According to the invention, each repressor-activator fusion protein is used in conjunction with a target promoter that is responsive to the particular fusion protein and that regulates transcription of an MDE-encoding sequence. Typically, the promoter comprises at least one operator sequence responsive to the repressor component of the repressor-activator fusion polypeptide, which is operably linked to at least a minimal promoter that supports transcription in eucaryotic cells. Examples of suitable repressor-responsive operator sequences include without limitation sequences derived from the tetracycline resistance operon encoded in Tn10 in *E. coli*, the lambda repressor operon, and the yeast GAL repressor operon. Examples of suitable eucaryotic promoters from which minimal promoters may be derived include without limitation the cytomegalovirus (CMV) IE promoter, PtK-1 (thymidine kinase) promoter, HSP (heat shock protein) promoter, and any eukaryotic promoter containing a TATA box. Minimal promoter sequences may be derived from these promoters by (i) creating deletion mutants using conventional methods and (ii) testing the ability of the resulting sequences to activate transcription in a cell line. U.S. Pat. No. 5,650,298 discloses a repressor-activator fusion protein comprised of sequences derived from the tetracycline repressor fused to VP16 sequences, which is designated tTA, and a tTA-responsive promoter, designated tet07, which comprises a Tn10-derived sequence linked to a portion of the CMV IE promoter.

Alternatively, temporal control is achieved by (i) expression in the transgenic animal of a heterologous or recombinant transcriptional activator polypeptide or polypeptides and (ii) the coupled use of a target promoter operably linked to an MMP-encoding sequence whose transcriptional activity is responsive to the heterologous or recombinant transcriptional activator. Useful transcriptional activators include without limitation a modified ecdysone receptor, in which a VP16 transactivation domain linked to the amino-terminal transactivation domain of the glucocorticoid receptor is fused to the ligand-binding domain and carboxyterminal sequence of the ecdysone receptor (No et al., *Proc. Natl. Acad. Sci. USA* 93:3346, 1996); a chimeric protein, designated pGL-VP, comprising VP16 activator sequences, GAL4 activation sequences, and a mutated human progesterone receptor ligand-binding domain (Wang et al., *Proc. Natl. Acad. Sci. USA* 91:8180, 1994; Wang et al., *Gene Therapy* 4:432, 1997); and chimeric proteins comprising transcriptional activators fused to estrogen (or other steroid) binding domains (Mattioni et al., *Meth. Cell Biol.* 43:335, 1994). The ecdysone receptor system utilizes retinoid X receptor (RXR) to form heterodimers with the chimeric receptor, and responds to ecdysone, muristerone (an ecdysone analogue) or dexamethasone. The pGL-VP system is responsive to mifepristone (RU486). Chimeric receptors containing an estrogen binding domain respond to hydroxytamoxifen (an estrogen analogue).

Spatial control of MDE expression is achieved by the use of transcriptional promoters that direct transcription selectively in joint tissues. Joint-specific expression as used herein refers to expression that is greater in joints than in other cells; typically, the level of expression in non-joint tissues is less than 10% of the level of expression in joints. Preferably, expression in non-joint tissues is undetectable. Useful promoter sequences that confer joint-specific expression on a sequence to which they are operably linked include without limitation sequences derived from the collagen type II promoter. It will be understood that a joint-specific promoter according to the invention may comprise one or more copies of particular sequences or sub-sequences, and these sequences may be in direct or inverted orientation relative to each other and relative to the sequence whose expression is regulated by the promoter.

Coordinated spatial and temporal control of MDE expression is preferably achieved by (i) placing expression of the repressor-activator fusion polypeptide or the transcriptional activator polypeptide under the control of a joint-specific promoter; (ii) placing the expression of the MDE or a derivative thereof under the control of a promoter responsive to the repressor-activator fusion polypeptide or the transcriptional activator polypeptide; and (iii) maintaining the transgenic animal during fetal development and early life under conditions in which MDE expression is repressed.

The method by which transgenic animals are maintained during fetal and early post-natal development so that MDE expression is repressed will depend on the particular transgenes being expressed. When a repressor-activator fusion polypeptide is used, repression is achieved by providing the animal with an agent that binds to the repressor-activator fusion protein and results in repression of transcription of the target MDE gene. In animals comprising a transgene encoding a repressor-activator fusion polypeptide containing tet repressor sequences, repression is achieved by providing tetracycline or a tetracycline analogue in the food or drinking water of the mother and, following birth, of the progeny. Tetracycline or an analogue may also be provided using surgically implanted subcutaneous time-release pellets (Innovative Research of America, Inc., Sarasota Fla.) In this case, binding of tetracycline or a tetracycline analogue to the repressor-activator fusion protein prevents the fusion protein from binding to, and activating transcription of, the cognate promoter. Tetracycline analogues are compounds closely related to tetracycline which bind to the tet repressor with a Ka of at least about $10^6 M^{-1}$, preferably with an affinity of about $10^9 M^{-1}$ or greater. Useful tetracycline analogues include without limitation doxycycline, anhdryrotetracycline, chlortetracycline, epioxytetracycline, and the like. The dosage used is one that will result in substantial repression of MMP expression. Typically, tetracycline or a tetracycline analogue is administered in the animal's drinking water at a dosage of about 1 mg/ml. When it is desired that MMPs be expressed, the tetracycline or analogue thereof is withheld.

In other embodiments, repression is achieved by withholding from the animal an agent required for activity of the transcriptional activator polypeptide. For example, if the transcriptional activator is a modified ecdysone receptor, the animals are maintained in the absence of ecdysone or an ecdysone analogue throughout fetal and early post-natal development. Ecdysone analogues are compounds closely related to ecdysone which bind to the modified ecdysone receptor with a Ka of at least about $10^6 M^{-1}$. Useful ecdysone analogues include without limitation muristerone A. When it is desired that MDEs be expressed, the animals are given, e.g., ecdysone or muristerone A via intraperitoneal injections at dosages of between about 10 mg and about 20 mg/animal. Similarly, when pGL-VP is used, activation is achieved by providing mifepristone.

In a preferred embodiment of the invention, a transgenic animal is constructed whose somatic and germline cells contain in stably integrated form two recombinant genes: (i) a first recombinant gene comprising a sequence encoding MMP-13*, wherein the sequence is operably linked to a tetO7 promoter; and (ii) a second recombinant gene encoding a tTA protein operatively linked to a collagen type II promoter. In this embodiment, animals are maintained in the presence of tetracycline or a tetracycline analogue throughout fetal and early post-natal development to repress the gene. Afterwards, tetracycline or the tetracycline analogue is withdrawn, and MMP-13 enzymatic activity is selectively expressed in joint tissues.

Animal Models for Cartilage-Degenerative Diseases

The present invention provides animal model systems in which phenotypic changes characteristic of cartilage-degenerative diseases, such as, e.g., joint or disc disease, are reproducibly exhibited. These diseases include without limitation osteoarthritis, rheumatoid arthritis, chondrodysplasias, and degenerative intervertebral disc diseases. The model systems of the invention exhibit one or more phenotypic indicators common to these diseases, which include without limitation loss of proteoglycan (as indicated by, e.g., loss of Safranin O staining) and cleavage of type II collagen in the affected tissues. The systems encompass the transgenic animals described above, in which recombinant or heterologous MDEs, particularly MMPs, are expressed in cartilage at a predetermined time in the life of the transgenic animal. The timing of the appearance of cartilage-degenerative indicators is determined by activating MDE expression and monitoring the effects on cartilage (see below). Preferably, one or more MDEs are expressed after birth, most preferably after the animal has reached adulthood.

Expression of the transgenes is typically monitored by extracting mRNA from different tissues and subjecting the extracted mRNA to one or more of the following: (i) reverse transcriptase-polymerase chain reaction (RT-PCR), using primers homologous to the transgene; (ii) RNAase protection; and (iii) Northern blot analysis. Alternatively, in situ hybridization may used.

The physiological effects of MDE expression on articular cartilage are monitored in test animals by sacrificing the animals and subjecting paraffin-embedded decalcified cartilage to staining with (i) hematoxylin and eosin (using conventional techniques) followed by double staining with (ii) Safranin O and fast green. Peter et al., *J. Dxp. Pathol.* 71:19, 1990. Alternatively, frozen sections may be obtained and stained with antibodies that are specific for cleavage fragments derived from type II collagen. Billinghurst et al., *J. Clin. Invest.* 99:1534, 1997. Typically, expression of the MMP transgene(s) for at least about 7 days results in detectable loss of proteoglycan and changes in growth plate morphology (see, e.g., Example 5 below). Animal models in which expression of MDEs, particularly MMPs, and most particularly an enzymatically active form of MMP-13, results in proteoglycan loss and/or cleavage of type II collagen are within the scope of the invention.

Other phenotypic indicators of cartilage-degenerative disease which can be monitored in transgenic animals produced according to the invention include without limitation gross observations of changes in joint function and histological evidence of (i) fibrillation and loss of articular cartilage and (ii) osteophyte formation.

Syndromes for which the transgenic animals of the invention provide useful models include without limitation any pathological condition that manifests a disturbance in the composition, morphology, and/or function of cartilage, including osteoarthritis; rheumatoid arthritis; degenerative intervertebral disc diseases; chondrodysplasias, including, e.g., Kniest dysplasia, achondrogenesis, and hypophosphatasia; and proteoglycan-mediated disorders, such as occur, e.g., in brachymorphic animals. Hall et al., *Cartilage: Molecular Aspects*, CRC Press, 1991, pp. 201–203.

In further embodiments of the invention, the transgenic animals can be subjected to additional treatments to modulate the cartilage-degenerative indicators and/or to supplement the animals' disease phenotype with additional physiological effects such as, e.g., those associated with a particular disease. For example, the transgenic animals may be further treated with inflammatory mediators to augment collagen degradation and/or induce loss of proteoglycan (see, e.g., Example 6 below). Furthermore, the timing and extent of MDE induction, with or without additional treatments, can be adapted to replicate the symptomatology of a particular disease or syndrome.

Methods for Evaluating Drugs that Modulate Degenerative Diseases of Cartilage

The present invention encompasses methods for discovery and evaluation of drugs and therapies for their efficacy against degenerative diseases of cartilage, particularly degenerative joint diseases. In one embodiment of the invention, the transgenic animals of the invention are maintained under conditions in which expression of one or more MDEs results in one or more phenotypic indicators of cartilage-degenerative disease. Once the symptoms have developed, the potential of a composition to counteract cartilage-degenerative disease can be evaluated by administering a known dose of the composition to the animal in which the symptoms have developed; monitoring the phenotypic indicators for a predetermined time following administration of the composition; and comparing the extent of the phenotypic indicators in the animal to which the composition was administered relative to a control animal. Control animals comprise age- and sex-matched transgenic animals that are maintained under an identical regimen (i.e., express the transgenes) but which do not receive the composition. Any statistically significant difference in the extent or nature of the phenotypic indicators indicates the potential of the composition to counteract cartilage-degenerative disease. As used herein, phenotypic indicators of cartilage-degenerative disease refer to proteoglycan loss, joint space narrowing, collagen degradation, and destruction of cartilage.

In another embodiment of the invention, the potential of a composition to counteract degenerative diseases of cartilage, particularly degenerative joint disease, is evaluated by administering to a transgenic animal a known dose of the composition before and/or simultaneous with the induction of MDE expression in the transgenic animal; monitoring phenotypic indicators of cartilage-degenerative disease for a predetermined time following administration of the composition and MDE induction; and comparing the extent of the phenotypic indicators and/or disease in the animal to which the composition was administered relative to a control animal that had not been exposed to the composition. In this embodiment, any statistically significant difference in the extent or nature of the phenotypic indicators and/or disease, or any statistically significant delay in appearance of the phentoypic indicators or disease, indicates the potential of the composition to counteract cartilage-degenerative disease.

A further indication of the potential of a composition to counteract cartilage-degenerative disease is the ability of the composition to cause any reduction in the extent or duration of other treatments, including, e.g., the dosage and timing of administration of other therapeutic agents used to alleviate symptoms of the disease.

Compounds that may be tested for anti-cartilage-degenerative disease potential may be found in, for example, natural product libraries, fermentation libraries (encompassing plants and microorganisms), combinatorial libraries, compound files, synthetic compound libraries, and compounds resulting from directed rational drug design and synthesis. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means. Blondelle et al., *TibTech* 14:60, 1996.

Transgenic animals

Transgenic animals as used herein refers to animals into which one or more heterologous and/or recombinant genes have been introduced. The transgenes may be from a different species, or from the same species as the transgenic animal but are not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that have been rearranged or mutated in vitro in order to alter the normal in vivo pattern of expression of the gene, or to alter or eliminate the biological activity of an endogenous gene product encoded by the gene. Also encompassed by the invention are DNA fragments that are introduced into a pre-existing gene to, e.g., change patterns of expression or to provide additional means of regulating the expression of the gene. Watson et al., "The Introduction of Foreign Genes Into Mice," in *Recombinant DNA*, 2d Ed., W.H. Freeman & Co., New York, 1992, pp. 255–272; Gordon, J. W., *Intl. Rev. Cytol.* 115:171,1989; Jaenisch, *Science* 240:1468, 1989; Rossant, Neuron 2:323, 1990.

The transgenic non-human animals of the invention are produced by introducing transgenes into the germline of the non-human animal. Embryonal target cells at various developmental stages are used to introduce the transgenes of the invention. Different methods are used depending on the stage of development of the embryonal target cell(s). Such methods include, but are not limited to, microinjection of zygotes, viral integration, and transformation of embryonic stem cells as described below.

1. Microinjection of zygotes is the preferred method for incorporating transgenes into animal genomes. A zygote, which is a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 picoliters of a solution containing transgenic DNA sequences. The use of a zygote for introduction of transgenes has the advantage that, in most cases, the injected transgenic DNA sequences will be incorporated into the host animal's genome before the first cell division. Brinster et al., *Proc. Natl. Acad. Sci. USA* 82:4438, 1985. As a consequence, all cells of the resultant transgenic animals (founder animals) stably carry an incorporated transgene at a particular genetic locus, referred to as a transgenic allele. The transgenic allele demonstrates Mendelian inheritance, i.e., half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the blastocyte developmental stage. The blastomeres may be infected with appropriate retroviruses. Jaenich, *Proc. Natl. Acad. Sci. USA* 73:1260. Infection of the blastomeres is enhanced by enzymatic removal of the zona pellucida. Transgenes are introduced via viral vectors which are typically replication-defective but which remain competent for integration of viral-associated DNA sequences, including transgenic DNA sequences linked to such viral sequences, into the host animal's genome. Transfection is easily and efficiently obtained by culture of blastomeres on a monolayer of cells producing the transgene-containing viral vector. Alternatively, infection may be performed using cells at a later developmental stage, such as blastocoeles. In any event, most transgenic founder animals produced by viral integration will be mosaics for the transgenic allele; that is, the transgene is incorporated into only a subset of all the cells that form the transgenic founder animals. Moreover, multiple viral integration events may occur in a single founder animal, generating multiple transgenic alleles which will segregate in future generations of offspring. Introduction of transgenes into germline cells by this method is possible but probably occurs at a low frequency. However, once a transgene has been introduced into germline cells by this method, offspring may be produced in which the transgenic allele is present in all of the animal's cells, i.e., in both somatic and germline cells.

3. Embryonal stem (ES) cells can also serve as target cells for introduction of the transgenes of the invention into animals. ES cells are obtained from pre-implantation embryos that are cultured in vitro. Evans et al., *Nature* 292:154, 1981. ES cells that have been transformed with a transgene can be combined with an animal blastocyst, after which the ES cells colonize the embryo and contribute to the germline of the resulting animal (which is a chimera, i.e., composed of cells derived from two or more animals). Again, once a transgene has been introduced into germline cells by this method, offspring may be produced in which the transgenic allele is present in all of the animal's cells, i.e., in both somatic and germline cells.

Although the initial introduction of a transgene is a Lamarckian (non-Mendelian) event, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

In practicing the invention, animals of the transgenic maintenance line are crossed with animals having a genetic background in which expression of the transgene results in symptoms of cartilage-degenerative disease. Offspring that have inherited the transgenes of the invention are distinguished from littermates that have not inherited transgenes by analysis of genetic material from the offspring for the presence of nucleic acid sequences derived from the transgenes of the invention. For example, biological fluids that contain polypeptides uniquely encoded by the transgenes of the invention may be immunoassayed for the presence of the polypeptides. A simpler and more reliable means of identifying transgenic offspring comprises obtaining a tissue sample from an extremity of an animal, such as, for example, a tail, and analyzing the sample for the presence of nucleic acid sequences corresponding to the DNA sequence of a unique portion or portions of the transgenes of the invention. The presence of such nucleic acid sequences may be determined by, e.g., hybridization ("Southern") analysis with DNA sequences corresponding to unique portions of the transgene, analysis of the products of PCR reactions using DNA sequences in a sample as substrates, oligonucleotides derived from the transgene's DNA sequence, and the like.

Nucleic Acids, Vectors, Expression Systems, and Polypeptides

The present invention encompasses isolated nucleic acids encoding MDEs, particularly MMPs, and enzymatically active fragments derived therefrom, as well as constitutively active MMP variants and enzymatically active fragments derived therefrom. The invention also encompasses complements of the above nucleic acids; vectors comprising the nucleic acids; cells comprising the vectors; and isolated polypeptides encoded by the nucleic acids.

Many techniques in molecular biology, microbiology, recombinant DNA, and protein biochemistry are used in practicing the present invention, such as those explained in, for example, Sambrook et al., 1989, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984, (M. L. Gait ed.); *Transcription and Translation*, 1984 (Hames and Higgins eds.); *A Practical Guide to Molecular Cloning*; the series, *Methods in Enzymology* (Academic Press, Inc.); and *Protein Purification: Principles and Practice*, Second Edition (Springer-Verlag, N.Y.).

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, such as, for example, DNA-DNA, DNA-RNA and RNA-RNA hybrids, as well as "protein nucleic acids" (PNA) formed by conjugating bases to an amino acid backbone. This also includes nucleic acids containing modified bases.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" of a nucleic acid sequence as used herein refers to the "antisense" sequence that participates in Watson-Crick base-pairing with the original sequence.

An "isolated" nucleic acid or polypeptide as used herein refers to a component that is removed from its original environment (for example, its natural environment if it is naturally occurring). An isolated nucleic acid or polypeptide typically contains less than about 50%, preferably less than about 75%, and most preferably less than about 90%, of the cellular components with which it was originally associated.

A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

Nucleic acids comprising any of the sequences disclosed herein or subsequences thereof can be prepared by conventional methods. For example, DNA can be chemically synthesized using, e.g., the phosphoramidite solid support method of Matteucci et al., 1981, *J. Am. Chem. Soc.* 103: 3185, the method of Yoo et al., 1989, *J. Biol. Chem.* 764:17078, or other well known methods. This can be performed by sequentially linking a series of oligonucleotide cassettes comprising pairs of synthetic oligonucleotides.

Due to the degeneracy of the genetic code, many different nucleotide sequences can encode polypeptides having the amino acid sequences defined herein or subsequences thereof. The codons can be selected for optimal expression in prokaryotic or eukaryotic systems. Such degenerate variants are also encompassed by this invention.

The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphbnates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also encompassed by the term "nucleic acid". The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The polypeptides of the invention may be expressed by using many known vectors, such as pUC plasmids, pET plasmids (Novagen, Inc., Madison, Wis.), or pRSET or pREP plasmids (Invitrogen, San Diego, Calif.), and many appropriate host cells, using methods disclosed or cited herein or otherwise known to those skilled in the relevant art. The particular choice of vector/host is not critical to the practice of the invention. Recombinant cloning vectors will often include one or more replication systems for cloning or expression; one or more markers for selection in the host, such as, for example, antibiotic resistance; and one or more expression cassettes. The inserted coding sequences may be synthesized by standard methods, isolated from natural sources, prepared as hybrids, or the like. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, fungal infection, microinjection, microprojectile, or other established methods.

Appropriate host cells include bacteria, archebacteria, fungi, yeast, plant, and animal cells, and especially mammalian cells. Of particular interest are *E. coli, S. aureus, B. subtilis, Saccharomyces cerevisiae, Saccharomyces carlsbergensis, Schizosaccharomyces pombi*, SF9 cells, C129 cells, 293 cells, *Neurospora*, CHO cells, COS cells, HeLa cells, and immortalized mammalian myeloid and lymphoid cell lines. Preferred replication systems include M13, ColE1, SV40, baculovirus, lambda, adenovirus, cytomegalovirus, and the like. A large number of transcription initiation and termination regulatory regions have been isolated and are effective in the transcription and translation of heterologous proteins in the various hosts. Examples of these regions, methods of isolation, manner of manipulation, etc. are known in the art (Ausubel et al., *Current Protocols in Molecular Biology*, John Wiley, 1997). Under appropriate expression conditions, host cells can be used as a source of recombinantly produced peptides and polypeptides.

The MDEs of the present invention, including function-conservative variants, may be isolated from native or heterologous organisms or cells (including, but not limited to, bacteria, fungi, insect, plant, and mammalian cells) into which the protein-coding sequence has been introduced and expressed. Alternatively, these polypeptides may be produced in cell-free protein synthesis systems, which may additionally be supplemented with microsomal membranes to achieve glycosylation and signal peptide processing of preprocollagenases. Furthermore, the polypeptides may be chemically synthesized by commercially available automated procedures, including, without limitation, exclusive solid phase synthesis, partial solid phase methods, fragment condensation, or classical solution synthesis.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible.

The construction and analysis of MMP variants and derivatives that exhibit enzymatic activity, and preferably constitutive enzymatic activity, can be achieved by routine application of conventional methods. First, a nucleic acid encoding an MMP is modified either by site-directed or random mutagenesis, or is used in a construction scheme as one segment of a fusion gene. Preferably, the procedure results in a modification either contained within the sequence encoding the pro region or near the pro region cleavage site; this includes deleting the pro region entirely. Alternatively, sequences may be constructed that encode fusion proteins either between enzymatically active MMP domains and other polypeptides, or between different MMPs. The modified nucleic acid is then used to program synthesis of a variant MMP, either in a cell-free system, in intact cells (including permeabilized cells), or in a transgenic animal. Preferably, either a cell-free system or a cell culture system is used to express the MMP variant or derivative. The extent of pro region cleavage is assessed by metabolic labelling and resolution of the MMP product by SDS-PAGE. Finally, MMP enzymatic activity is measured using conventional assays, such as, by quantifying the cleavage of natural substrates or model peptides, as disclosed, e.g., in Weingarten et al., *Biochem.* 24:6730, 1985; Woessner et al., *J. Biol. Chem.*, 263:16918, 1988, and Knight et al., *FEBS Letts.*, 296:263, 1992. In this manner, a large number of MMP variants and derivatives, including, e.g., function-conservative variants of MMP-13*, can be created routinely and assayed for MMP enzymatic activity.

DESCRIPTION OF THE PREFERRED EMBODIMENTS

The following examples are intended to illustrate the present invention without limitation.

Example 1

Construction of a Gene Encoding a Modified, Constitutively Active ProMMP-13

The following experiments were performed to create a gene encoding a procollagenase derived from MMP-13 that is enzymatically active in the absence of pro region cleavage. The sequence of this proMMP-13 variant, designated MMP13*, is shown in FIG. 1B, SEQ ID NO: 1.

Site-directed mutagenesis was performed to modify MMP-13 cDNA as follows:

A cDNA fragment encoding proMMP was obtained by digesting plasmid pNot3A (Freije et al., *J. Biol. Chem.* 269:16766, 1994; GENBANK accession number X75308) with XbaI and HindIII and purifying the resulting ~1515 bp fragment. This fragment was subcloned into the Tet-resistant/Amp-sensitive pAlter plasmid (Promega, Madison, Wis.) that had been digested with XbaI and HindIII.

Site-directed mutagenesis was performed using the Altered Sites II in vitro Mutagenesis System (Promega, Madison, Wis.). Briefly, phagemid single-stranded DNA was purified from cultures containing the helper phage R408 (Promega). In addition to the Amp repair—Tet knock-out conversion oligos (Promega), an oligonucleotide having the sequence 5'-AAGCCAAGATGCGGGGTTGTCGAT-GTGGGTGAATACAAT-3', SEQ ID NO:5, was phosphorylated and annealed to the single-stranded DNA, followed by mutant strand synthesis. The reaction mixture was then used to transform the repair-minus E. coli strain ES1301 mutS, and the culture was grown in ampicillin selective media. Plasmid DNA was isolated from isolated clones and transformed into JM109 cells, which were then plated on LB plates containing 120 µg/ml ampicillin.

The above procedure resulted in a proline-to-valine substitution at amino acid 99. The modified proMMP was designated MMP13* (FIG. 1B, SEQ ID NO: 1).

Using a similar technique, site-directed mutagenesis was also used to introduce a valine to glycine mutation at amino acid 98. A mutagenic oligonucleotide having the sequence 5'-GAAAAAGCCAAGATGCGGGGGTCCTGAT-GTGGGTGAATAC-5', SEQ ID NO:6 was used as described above. This procedure resulted in a valine-to-glycine substitution at amino acid 98.

After confirmation of the above mutations by direct sequencing, cDNA encoding MMP13* cDNA was excised from the pAlter vector by digestion with Eco RI and Hind III.

The enzymatic activity of MMP-13* was determined as follows:

1. cDNAs encoding both mutant forms of MMP13 and wild-type MMP-13 were subcloned into a BS(SK-) vector (Stratagene) containing the CMV promoter (Xho 1-Eco RI) and the SV40 splice poly $(A)_n$ (Xba I–Nco I). Duplicate cultures of Hela cells (10 cm dishes) were transfected with 50 µg of these plasmids using the $CaPO_4$ precipitation method (Promega). Five hours later, cells were subjected to a 1-minute glycerol shock using a solution containing an equal volume of 2×HBS+30% glycerol. This procedure is described in the Profection Mammalian Transfection Systems technical manual (Promega).

2. Twenty-four hours following transfection, the culture medium (D-MEM containing 10% fetal bovine serum) was replaced with D-MEM containing no serum and 10 µM CGS-27023A (Ciba-Geigy), an MMP inhibitor. It is believed that, in the absence of an added MMP inhibitor, MMPs produced by the culture autodigest; thus, addition of an MMP inhibitor to the culture medium resulted in a detectable MMP13 band.

3. Forty-eight hours after the addition of serum-free medium containing the MMP inhibitor, 10 ml of supernatant were collected and concentrated about 200-fold using Centriprep-30 and Centricon-10 concentrators (Amicon), after which an equal volume of 2×Tris-glycine SDS running buffer was added to each sample. The samples were then applied to a 4–16% pre-stained beta-casein zymogram SDS polyacrylamide gel (Novex). After electrophoresis, the gels were renatured in renaturing buffer (Novex) for 30 minutes at room temperature, followed by overnight incubation at 37° C. in zymogram developing buffer (Novex).

The results indicated that cells expressing either a variant MMP13 containing a proline→valine substitution at position 99 (MMP-13*) or a variant MMP13 containing a valine→glycine substitution at position 98 secreted detectable MMP activity similar to cells expressing wild-type MMP-13. This method thus provides a rapid screen for MMP13 variants that retain MMP13 enzymatic activity.

In a further step, cDNA encoding MMP-13* was operably linked to a transcriptional regulatory sequence derived from the tet07 promoter as follows:

1. The BS(SK-) vector (Stratagene) was digested with KpnI and NotI. A synthetic duplex oligonucleotide having the following sequence was digested with KpnI and Not I and ligated to the vector:

5'-GGTACCACTAGTAAGCTTAGATCT-CATATGGTCGACCCCGGGGAATTCCTGCA GGGATC-CTCTAGAAGTACTCCATGGGTATACATC-GATGCGGCCGC-3', SEQ ID NO:7

The SB(SK-) vector as modified above was digested with XbaI and NcoI. A 745 bp fragment containing the SV40 splice site and polyadenylation signal, which was obtained by digesting pcDNAI/Amp (Invitrogen, Carlsbad, Calif.) with XbaI and NcoI, was ligated to this vector. This 745 bp fragment was recovered by digestion of the vector with XbaI and NotI and was inserted into the original BS(SK-) vector.

2. The resulting vector was linearized by digestion with XhoI and EcoRI and ligated to a 460 bp XhoI-EcoRI fragment containing the tetO7 promoter region (Gossen et al., *Proc. Natl. Acad. Sci. USA* 89:5547, 1992). This vector was then digested with SpeI, blunt-ended with Klenow polymerase, and digested with EcoRI.

3. pAlter-MMP13* was digested with HindIII, blunt-ended with Klenow polymerase, and digested with EcoRI to obtain an MMP13*-encoding fragment.

4. The MMP13* EcoRI fragment was cloned into the EcoRI digested vector obtained in step 2.

5. The 2792 bp transgene, SEQ ID NO:8, was excised by digestion with XhoI and NotI and purified using CsCl gradient centrifugation.

Example 2

Construction of a Collagen Type II-Promoter-Linked tTa Gene

The following experiments were performed to create a gene encoding a tTA repressor-activator fusion protein operably linked to a joint-specific (type II collagen) promoter as well as a reporter gene suitable for assessing the tissue-specific expression conferred by the type II collagen promoter.

1. Type II collagen promoter—tetracycline/VP16 transgene: The modified BS(SK-) vector containing the SV40 splice site and polyadenylation signal as described in Example 1 above was digested with NdeI and Sma I and ligated to a 1897 bp fragment containing the collagen II promoter and enhancer. This fragment was obtained by digesting plasmid PBSΔH1 with HindIII, after which it was blunt-ended with Klenow and digested with NdeI.

The plasmid was then digested with EcoRI and BamHI and ligated to a 1025 bp fragment encoding the tetracycline/VP16 repressor-activator fusion protein that had been excised from the pUHG15-1 plasmid (Gossen et al., *Proc. Natl. Acad. Sci. USA* 89:5547, 1992) using EcoRI and BamHI. The plasmid was linearized by digestion with BglII, dephosphorylated using calf intestinal phosphatase, and ligated to a 1554 BamHI enhancer fragment obtained from plasmid PBSΔH1.

Finally, the 5276 bp transgene, SEQ ID NO:9, was excised from the vector by digestion with KpnI and NotI, gel purified, purified by CsCl gradient centrifugation, dialyzed against microinjection buffer (5 mM Tris-HCl pH 7.4, 0.1 mM EDTA pH 8.0) and used for microinjection (see Example 3 below).

2. Type II collagen promoter-β-galactosidase gene: A 4179 bp BamHI-BglII fragment containing the β-galactosidase gene fused to the β-globin splice sequence and polyadenylation signal was excised from plasmid pUGH16-3 (Gossen et al., *Proc. Natl. Acad. Sci. USA* 89:5547, 1992) and cloned into the BamHI site of unmodified BS(SK-) (Stratagene). This plasmid was digested with EcoRI and HindIII and ligated to a 655 bp Hind III-Eco RI fragment containing the type II collagen promoter sequence, which was excised from the plasmid described in (1) above. The plasmid was then digested with EcoRI and ligated to a 2807 bp Eco RI fragment which had been excised from the type II collagen promoter plasmid described above. Restriction mapping was used to verify the orientation of each insert. The 7664 bp transgene, SEQ ID NO:10, was excised by digestion with HindIII and NotI, gel purified, purified by CsCl gradient centrifugation, dialyzed against microinjection buffer (5 mM Tris pH 7.4, 0.1 mM EDTA pH 8.0), and microinjected into mouse embryos.

Example 3

Production and Characterization of Transgenic Mice Expressing Tetracycline-Regulated MMP-13 in Joint Tissues The following experiments were performed to produce transgenic mice expressing MMP-13* or a LacZ (β-galactosidase) reporter gene.

Figure 2:
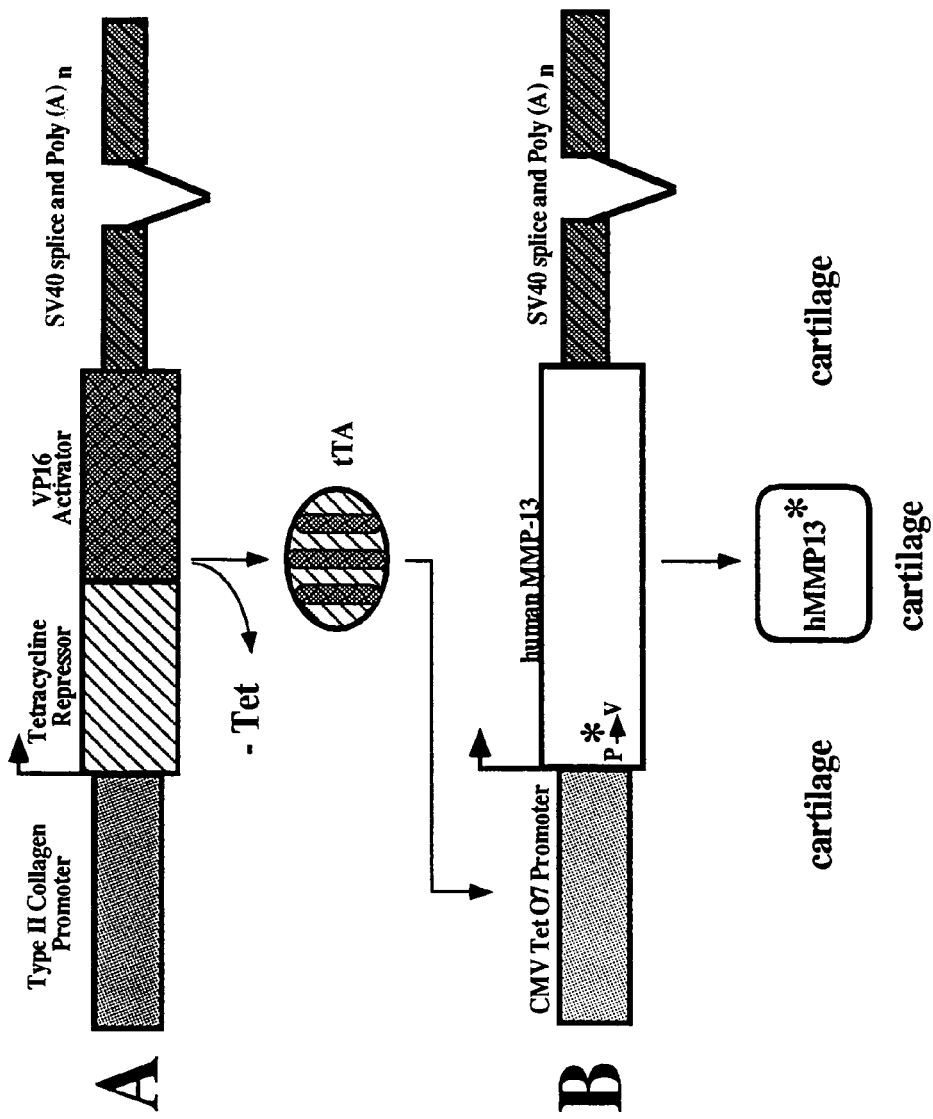
FIGS. 2A and 2B are schematic illustrations of transgenes used for regulated expression of human MMP-13* in transgenic mice.

To produce mice expressing MMP-13* under tetracycline regulation, an XhoI-NotI tet07-MMP-13* DNA fragment (FIG. 2B, SEQ ID NO:8) and a KpnI-NotI CPE-tTA DNA fragment (FIG. 2A, SEQ ID NO:9) were co-microinjected into fertilized mouse embryos in equimolar amounts. To produce mice expressing the reporter gene, a HindIII-NotI LacZ fragment (described in Example 2 above) was injected into (FVB/N) fertilized eggs as described (Hogan et al., *Manipulating the Mouse Embryo*, Cold Spring Harbor Laboratories, 1996).

Founder animals were first identified by PCR as follows. The tTA-encoding transgene was identified using a primer corresponding to the tTA sequence (5'-CGAGGGCCT-GCTCGATCTCC-3', SEQ ID NO:11) and a primer corresponding to a 3' untranslated sequence (5'-GGCATTCCAC-CACTGCTCCC-3', SEQ ID NO:12). The resulting PCR product was 584 bp in size. The MMP13* —encoding transgene was identified using primers corresponding to sequences encoding MMP13* (5'-GAGCACCCTTCTCAT-GACCTC-3', SEQ ID NO:13) and the 3' untranslated region, respectively. The resulting PCR product was 731 bp in size. Out of 112 newborn mice, 7 transgenic founders harboring both transgenes were found.

The LacZ-encoding transgene was identified using primers corresponding to the nuclear localization signal of the β-galactosidase gene (5'-GTTGGTGTAGATGGGCG-CATCG-3', SEQ ID NO: 14) and the collagen promoter (5'-GCGGGGTCTCAGGTTACAGCC-3', SEQ ID NO: 15). The resulting PCR product was 673 bp in size.

Southern blot analysis of tail DNA digested with BamHI/NcoI or PvuII/NcoI and hybridized to the 3' untranslated region under high stringency conditions was performed to confirm the results obtained using PCR. The number of copies of transgene DNA that integrated into the genome was determined by comparing the relative intensity of the hybridization signal from transgenic mice with that obtained using control DNAs containing 10 and 100 genome equivalents of the same DNA that was injected. Transgenic lines were generated by mating founder animals to FVB/N wild type animals.

All mice were administered doxycycline (Sigma Chemical Co., St. Louis Mo.) at a concentration of 1.0 mg/ml in acidic drinking water, which was changed on a daily basis. Schultze et al., *Nature Biotech.* 14:499, 1996.

Example 4

Analysis of Joint-Specific Expression Conferred by Type II Collagen Promoter Constructs The following experiments were performed to evaluate tissue-specific expression conferred by use of the type II collagen promoter.

Joint-specific expression was monitored by staining for β-galactosidase activity as described (Hogan et al., *Manipulating the Mouse Embryo*, Cold Spring Harbor Laboratories, 1996); using this method, the presence of enzymatically active β-galactosidase is reflected in the appearance of a blue stain.

Wild-type female mice were mated with transgenic males harboring the CPE-LacZ construct as described in Examples 2 and 3 above. On embryonic day 16, the females were sacrificed, and the embryos were stained for β-galactosidase activity. Prior to fixation, the tails were removed from the embryos and used as a source of template DNA for PCR reactions to determine transgene transmission.

Figure 3:
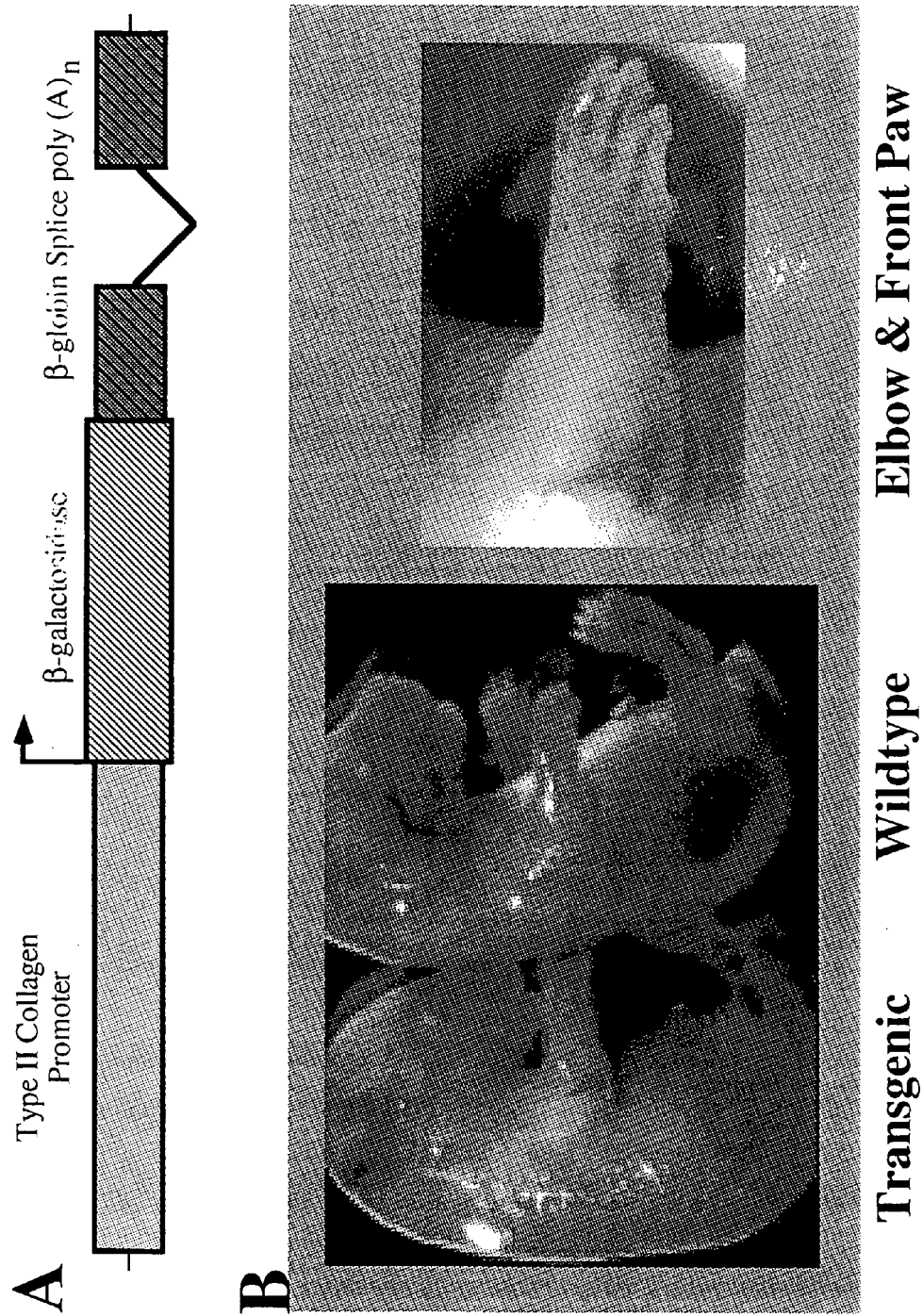
FIG. 3A is a schematic illustration of a transgene used to assess tissue-specific regulation conferred by a type II collagen promoter. The nucleic acid construct comprises, in a 5' to 3' direction: (i) sequences derived from a rat type II collagen promoter; (ii) sequences encoding bacterial β-galactosidase (LacZ); and (iii) sequences comprising an SV40-derived RNA splice site and polyadenylation signal.
FIG. 3B is a color photographic illustration of whole mount staining for β-galactosidase activity of embryonic day 16 transgenic mouse embryos expressing the transgene illustrated in FIG. 3A. Blue staining, indicating the presence of enzymatically active B-galactosidase polypeptides, is evident in joints throughout the body of the transgenic animal, while no staining is observed in the non-transgenic, wild-type littermate.

FIG. 3B illustrates the blue staining that is observed in joints throughout the body of the embryonic day 16 transgenic mouse embryo. Specifically, β-galactosidase expression was observed in ankles, knees, hips, phalanges, wrists, elbows, shoulders, and vertebrae. In addition to the cartilage of the joints, cartilage that had not ossified to bone at this stage of development, i.e., some of the facial, skull, and rib bones, also expressed β-galactosidase. No staining was observed in non-transgenic, wild type littermates.

These results indicated that the type II collagen-derived promoter according to the present invention is capable of conferring joint-specific expression on sequences to which it is operably linked.

Example 5

Analysis of the Phenotypic Effects of Joint-Specific Expression of MMP-13*

The following experiments were performed to evaluate the development of phenotypic indicators of cartilage degeneration in transgenic animals expressing MMP-13* in joint tissue.

Mice harboring both the tet07-MMP-13* and CPE-tTA constructs (produced as described in Example 3 above) were maintained on doxyciline until adulthood (approximately 8 weeks postpartum).

Expression of MMP13* was first evaluated in hemizygous mice using RT-PCR to detect the transcripts. No expression of the transgene was observed in any of the lines in any of the tissues sampled, including brain, heart, liver, kidney, hindlimb, muscle, bone, or tongue.

To examine whether MMP-13* DNA in any of the double-transgenic lines was capable of being expressed, embryonic fibroblasts were prepared from these animals and transfected with a tTA expression plasmid (Gossen and Bujard, *Proc. Natl. Acad. Sci. USA* 89:5547, 1992). The transfection was done because the joint-specific type II collagen promoter regulating tTA expression (and thereby MMP13* expression) in the transgenic animals might not be expected to function in embryonic fibroblasts.

For this purpose, wild-type females were mated to transgenic males harboring both the type II collagen promoter-linked tTA and Tet07-MMP-13* transgenes. On embryonic day 15, the females were sacrificed, and fibroblasts were prepared from the embryos (Graham et al., *Virol.* 52:456, 1973; Lopata et al., *Nuc. Acid Res.* 12:5707, 1984). The fibroblasts were cultured in DMEM containing 10% fetal bovine serum, and were transfected with the tTa expression plasmid using the calcium phosphate method. Forty-eight hours after transfection, total RNA was prepared from the cells using the Trizol method (GIBCO/BRL, Grand Island, N.Y.). RT-PCR was performed using the Superscript preamplification system (GIBCO/BRL) for first-strand cDNA, after which MMP-13* sequences were detected by PCR using the following MMP-13*-specific primers: 5'-GC-CCTCTGGCCTGCTGGCTCATG-3', SEQ ID NO: 16 and 5'-CAGGAGAGTCTTGCCTGTATCCTC-3', SEQ ID NO: 17.

Fibroblasts from several transgenic lines (such as, e.g., lines 8 and 42) were capable of expressing MMP13*, as evidenced by the appearance of a PCR product of the predicted size. No MMP13* RT-PCR band was detected from cells transfected with vehicle alone. These results indicated that, in these mice, the MMP13* transgene is integrated into a transcriptionally active region of the chromatin.

Expression of MMP13* in the double transgenic lines was further analyzed by immunohistochemistry, using antibodies specific for MMP-13-derived type II collagen cleavage fragments. For this purpose, joints were fixed in 4% paraformaldehyde in PBS at neutral pH for 60 minutes at room temperature. They were then rinsed twice in PBS, incubated in 0.1M Tris-HCl, pH 7.4, overnight, and partially decalcified in 0.2M EDTA at neutral pH. The samples were transferred to TOC medium and 6-mm frozen sections were obtained using a Hacker/Bright cryostat. The sections were stained with an antibody that recognizes an epitope present in a degradation product of type II collagen, specifically, in the $TC^A$ degradation product, which is also designated the ¾ piece. Billinghurst et al., *J. Clin. Invest.* 99:1534, 1997.

Figure 4:
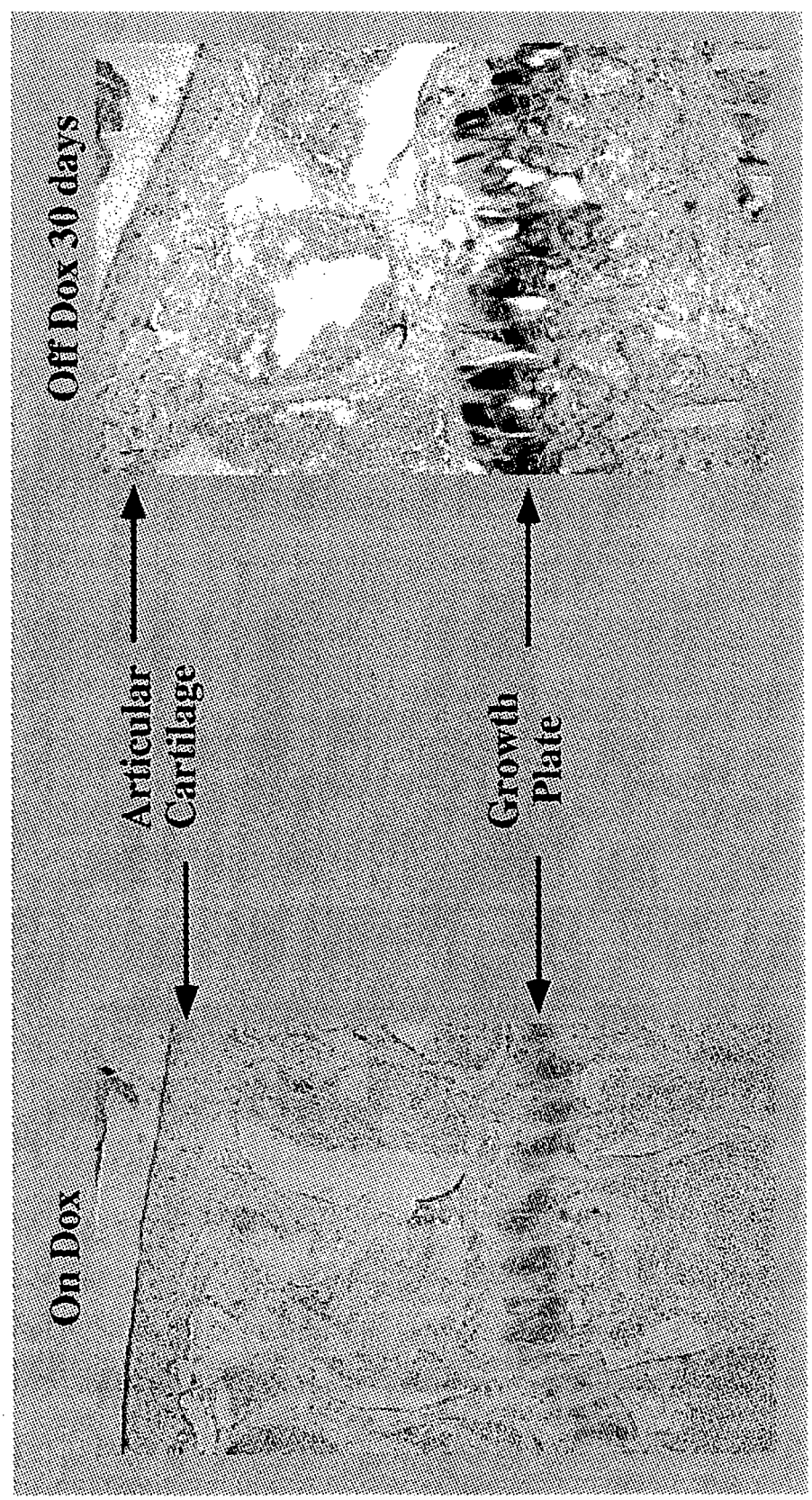
FIG. 4 shows color photographic illustrations of immunohistochemical localization of type II collagen cleavage products in the growth plate and articular cartilage of transgenic mice expressing the transgenes shown in FIG. 2. The tissues were stained with an antibody that recognizes cleavage products of type II collagen. The left panel shows tissue derived from a mouse that had been maintained on doxycycline to repress MMP-13* expression. The right panel shows tissue derived from a mouse that had been withdrawn from doxycycline, allowing expression of MMP-13*, for 30 days at 3 months of age.

As early as 3 days after removal of the mice from doxycycline, MMP-13 cleavage products could be detected. After 30 days without doxycycline, a substantial increase in staining in the growth plate and in the articular cartilage could be seen (FIG. 4), but the results differed among different lines of mice (see Table 1 below).

TABLE 1

| F1 Animal | Days off Dox | Immunohistochemistry | | Loss of Safranin O Stain |
|---|---|---|---|---|
| | | hMMP13 Ab | Type II Collagen Cleavage Fragments Ab | |
| Line 8 | wt | − | − | not remarkable |
| Line 8 | 0 d | − | − | " |
| | 3 d | + | + | " |
| | 7 d | ++ | ++ | Mild |
| | 14 d | +++ | +++ | Moderate |
| | wt | − | − | not remarkable |
| Line 6 | 30 d | | | Moderate |
| Line 8 | 30 d | +++ | +++ | Moderate |
| Line 42 | 30 d | + | − | not remarkable |

To study the effect of MMP13* activity on cartilage in adult transgenic animals, mice were withdrawn from doxycycline for increasing times, after which they were sacrificed. Paraffin-embedded formaldehyde-fixed sections of decalcified cartilage were sectioned and stained with (i) hematoxylin and eosin and (ii) Safranin O followed by fast green (American Histo Labs, Gaithersburg Md.). Peter et al., *J. Exp. Pathol.* 71: 19, 1990.

Figure 5:
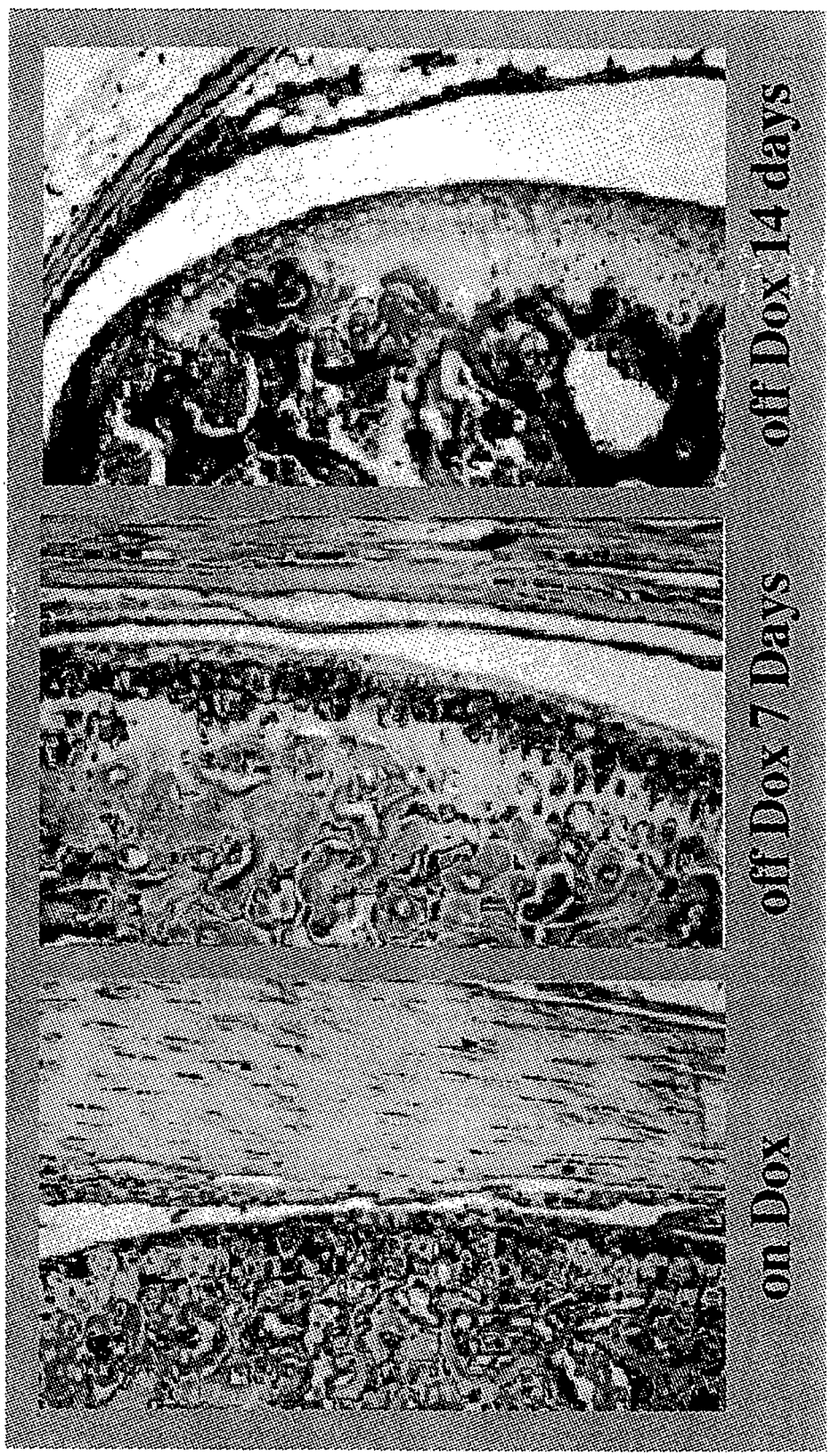
FIG. 5 is a color photographic illustration of Safranin O staining of the articular cartilage and growth plate of the patella of double transgenic mice. The left panel shows tissue derived from a mouse maintained on doxycycline. The middle panel shows tissue derived from a mouse 7 days after withdrawal from doxycycline. The right panel shows tissue derived from a mouse 14 days after withdrawal from doxycycline.

Control transgenic animals that lack MMP13* expression retain a significant amount of safranin O stain in both the articular cartilage as well as the growth plate of their patella (FIG. 5, left panel). By contrast, transgenic animals from line 8 show a substantial loss of safranin O staining in their joints following doxycyline withdrawal. After seven days, a mild reduction of safranin O staining is observed in the articular cartilage of the patella (FIG. 5, middle panel), which progresses by day 14 to moderate loss of stain in articular cartilage as well as the growth plate (FIG. 5, right panel). A significant loss of safranin O stain was also observed in the other joints including the cartilage of the tarsus and femur, as well as wrist and knuckle, indicating a reduced proteoglycan concentration in these areas compared to controls.

Example 6

Augmentation of the Development of Symptoms of Joint Degenerative Disease in MMP-13 Transgenic Mice The following treatments are performed to enhance the symptoms of joint degeneration exhibited by the transgenic animals of the invention.

A group of transgenic mice are treated to induce expression of the transgenes at 4–12 weeks of age. Two to six weeks after induction, the mice are injected intraperitonealy with an inflammatory agent, including without limitation, lipopolysaccharide (10–100 µg), zymosan (1–10 mg), the superantigen Staphylococcal Enterotoxin B (1–100 µg), or TGF-β (1–10 µg). Alternatively, the animals are injected intraarticularly with an inflammatory or chondrocyte function-modulating agent, including without limitation, lipopolysaccharide (1–100 ng), zymosan (50–250 µg), papain (10–100 µg), TGF-β (0.01–1 µg), Bone Morphogenic Protein-2 (2–1000 ng), IL-1 (1–100 ng), TGF-α (10–200 ng), IGF (0.01–1 µg), or FGF (0.01–1 µg). Age- and sex-matched transgenic mice maintained under a regimen in which the transgenes are not expressed receive the same treatment and serve as controls.

The development of symptoms of degenerative joint disease is monitored by gross observation of joint swelling and function, and by histological evaluation of the joint at selected timepoints after exposure to the inflammatory agent.

The agents will induce an acute inflammatory response and/or transient loss of proteoglycan with a duration of less than one week. The acute inflammatory response and/or transient cartilage changes will upregulate gene expression in the chondrocytes, enhancing the expression of the transgene and increasing the levels of MMP-13 produced.

All patents, applications, articles, publications, and test methods mentioned above are hereby incorporated by reference in their entirety.

Many variations of the present invention will suggest themselves to those skilled in the art in light of the above detailed description. Such obvious variations are within the full intended scope of the appended claims.

---

The invention claimed is:

1. A transgenic rat whose genome comprises:
   (a) a nucleotide sequence encoding a constitutively enzymatically active human matrix metalloproteinase that cleaves Type II collagen, wherein the nucleotide sequence encoding the metalloproteinase is operatively linked to a regulatable promoter; and
   (b) a nucleotide sequence encoding a repressor-activator fusion polypeptide that binds to the regulatable promoter in the absence of a repressor-activator fusion polypeptide-binding compound and does not bind to the regulatable promoter in the presence of the compound, which nucleotide sequence encoding the repressor-activator fusion polypeptide is operatively linked to a chondrocyte-specific promoter,
   wherein expression of the metalloproteinase is capable of being repressed in the rat until adulthood, and wherein the metalloproteinase is capable of being expressed in the rat during adulthood to a level sufficient to cause Type II collagen degradation in the joints of the rat.

2. The transgenic rat of claim 1, wherein the matrix metalloproteinase is selected from the group consisting of MMP-1, MMP-8, and MMP-13.

3. The transgenic rat of claim 2, wherein the matrix metalloproteinase is MMP-13.

4. The transgenic rat of claim 3, wherein the MMP-13 comprises the sequence of SEQ ID NO: 1 or SEQ ID NO:21.

5. The transgenic rat of claim 1, wherein the repressor-activator fusion polypeptide is a chimeric tetracycline repressor-VP16 transcription activator polypeptide and the regulatable promoter is a Tn10 sequence linked to a portion of the CMV IE promoter.

6. The transgenic rat of claim 5, wherein the regulatable promoter comprises the sequence of SEQ ID NO:2.

7. A method for evaluating the potential of a composition to counteract degradation of Type II collagen in joints of a transgenic rat, which degradation results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:
   (a) providing a first and second transgenic rat of claim 5;
   (b) activating expression of the metalloproteinase at the same age during adulthood of the transgenic rats, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;
   (c) administering the composition to the first transgenic rat; and
   (d) comparing the phenotype of the first transgenic rat to which the composition was administered with the phenotype of the second transgenic rat in which the composition was not administered,
   wherein any less extensive development in the nature or extent of the phenotype in the first transgenic rat or any increased length of time required for the phenotype to develop in the first transgenic rat that has been administered the composition relative to the phenotype in the second transgenic rat, indicates the potential of the composition to counteract degradation of Type II collagen in joints.

8. The transgenic rat of claim 1, wherein the Type II collagen degradation results in a loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, or combinations thereof.

9. The transgenic rat of claim 1, wherein the chondrocyte-specific promoter is a Type II collagen promoter.

10. A method for producing degradation of Type II collagen in the joints of a transgenic rat, which method comprises:
   (a) maintaining the transgenic rat of claim 1 in presence of the transcription activator protein-binding compound until adulthood; and
   (b) activating expression of the matrix metalloproteinase in the transgenic rat by withholding the compound from the rat after the rat has reached adulthood such that the matrix metalloproteinase degrades Type II collagen in the joints of the transgenic rat.

11. The method according to claim 10, wherein the Type II collagen degradation results in a loss of proteoglycan, cleavage of type II collagen into a TCA degradation product, a change in joint function, joint space narrowing, destruction of cartilage, a change in growth plate morphology, fibrillation and loss of articular cartilage, osteophyte formation, or combinations thereof.

12. A method for evaluating the potential of a composition to counteract degradation of Type II collagen in joints of a transgenic rat, which degradation results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:
   (a) providing a first and second transgenic rat of claim 1
   (b) activating expression of the metalloproteinase at the same age during adulthood of the transgenic rats, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;
   (c) administering the composition to the first transgenic rat; and
   (d) comparing the phenotype of the first transgenic rat to which the composition was administered with the phenotype of the second transgenic rat in which the composition was not administered,
   wherein any less extensive development in the nature or extent of the phenotype in the first transgenic rat or any increased length of time required for the phenotype to develop in the first transgenic rat that has been administered the composition relative to the phenotype in the second transgenic rat, indicates the potential of the composition to counteract degradation of Type II collagen in joints.

13. A transgenic rat whose genome comprises:
   (a) a nucleotide sequence encoding a constitutively enzymatically active human matrix metalloproteinase that cleaves Type II collagen, wherein the nucleotide sequence encoding the metalloproteinase is operatively linked to a tetracycline-regulatable promoter; and
   (b) a nucleotide sequence encoding a repressor-activator fusion polypeptide that binds to the tetracycline regulatable promoter in the absence of tetracycline or a tetracycline analog and does not bind to the regulatable promoter in the presence of tetracycline or tetracycline analog, which nucleotide sequence encoding the repressor-activator fusion polypeptide is operatively linked to a chondrocyte-specific promoter,
   wherein expression of the metalloproteinase is capable of being repressed in the rat until adulthood, and wherein the metalloproteinase is capable of being expressed in the rat during adulthood to a level sufficient to cause Type II collagen degradation in the joints of the rat.

14. The transgenic rat of claim 13, wherein the matrix metalloproteinase is constitutively enzymatically active MMP-13, the tetracycline-regulatable promoter is tet07, the repressor-activator fusion polypeptide is tTA, and the chondrocyte-specific promoter is a Type II collagen promoter.

15. The transgenic rat of claim 13, wherein the Type II collagen degradation results in a loss of proteoglycan, cleavage of type II collagen into a TCA degradation product, a change in joint function, joint space narrowing, destruction of cartilage, a change in growth plate morphology, fibrillation and loss of articular cartilage, osteophyte formation, or combinations thereof.

16. A method for producing degradation of Type II collagen in the joints of a transgenic rat, which method comprises
   (a) maintaining the transgenic rat of claim 13 in the presence of tetracycline or a tetracycline analog until adulthood; and
   (b) activating expression of the matrix metalloproteinase by withholding the tetracycline or tetracycline analog from the rat after the rat has reached adulthood, such that the matrix metalloproteinase degrades Type II collagen in the joints of the transgenic rat.

17. The method according to claim 16, wherein the tetracycline analog is doxycycline.

18. The method according to claim 16, wherein the Type II collagen degradation results in a loss of proteoglycan, cleavage of type II collagen into a TCA degradation product, a change in joint function, joint space narrowing, destruction of cartilage, a change in growth plate morphology, fibrillation and loss of articular cartilage, osteophyte formation, or combinations thereof.

19. A method for evaluating the potential of a composition to counteract degradation of Type II collagen in joints of a transgenic rat, which degradation results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:
   (a) providing a first and second transgenic rat of claim 13;
   (b) activating expression of the metalloproteinase at the same age during adulthood of the transgenic rats, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;

(c) administering the composition to the first transgenic rat; and (d) comparing the phenotype of the first transgenic rat to which the composition was administered with the phenotype of the second transgenic rat in which the composition was not administered, wherein any less extensive development in the nature or extent of the phenotype in the first transgenic rat or any increased length of time required for the phenotype to develop in the first transgenic rat that has been administered the composition relative to the phenotype in the second transgenic rat, indicates the potential of the composition to counteract degradation of Type II collagen in joints.

20. A transgenic non-human rat whose genome comprises:

(a) a nucleotide sequence encoding a constitutively enzymatically active human matrix metalloproteinase that cleaves Type II collagen, wherein the nucleotide sequence encoding the metalloproteinase is operatively linked to a regulatable promoter; and (b) a nucleotide sequence encoding a transcription activator protein that binds to the regulatable promoter in the presence of a transcription activator protein-binding compound and does not bind to the regulatable promoter in the absence of the compound, which nucleotide sequence encoding the transcription activator protein is operatively linked to a chondrocyte-specific promoter;

wherein expression of the metalloproteinase is capable of being repressed in the rat until adulthood, and wherein the metalloproteinase is capable of being expressed in the rat during adulthood to a level sufficient to cause Type II collagen degradation in the joints of the rat.

21. The transgenic rat of claim 20, wherein the matrix metalloproteinase is selected from the group consisting of MMP-1, MMP-8, and MMP-13.

22. The transgenic rat of claim 21, wherein the matrix metalloproteinase is MMP-13.

23. The transgenic rat of claim 22, wherein the MMP-13 comprises the sequence of SEQ ID NO:1 or SEQ ID NO:21.

24. The transgenic rat of claim 20, wherein the chondrocyte-specific promoter is a Type II collagen promoter.

25. The transgenic rat of claim 20, wherein the transcription activator protein is a chimeric polypeptide comprising a transactivator domain linked to an ecdysone receptor ligand-binding domain, and wherein the transgenic rat further comprises a nucleotide sequence encoding a retinoid X receptor (RXR), which nucleotide sequence encoding RXR is operatively linked to a chondrocyte-specific promoter.

26. A method for producing degradation of Type II collagen in the joints of a transgenic rat, which method comprises:

(a) maintaining the transgenic rat of claim 25 in the absence of ecdysone, an ecdysone analog, or dexamethasone until adulthood; and (b) activating expression of the matrix metalloproteinase in the transgenic rat by administering ecdysone, an ecdysone analog, or dexamethasone to the rat after the rat has reached adulthood such that the matrix metalloproteinase degrades Type II collagen in the joints of the rat.

27. The method according to claim 26, wherein the Type II collagen degradation results in a loss of proteoglycan, cleavage of type II collagen into a TCA degradation product, a change in joint function, joint space narrowing, destruction of cartilage, a change in growth plate morphology, fibrillation and loss of articular cartilage, osteophyte formation, or combinations thereof.

28. A method for evaluating the potential of a composition to counteract degradation of Type II collagen in joints of a transgenic rat, which degradation results in a phenotype selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:

(a) providing a first and second transgenic rat of claim 25;

(b) activating expression of the metalloproteinase at the same age during adulthood of the transgenic rats, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;

(c) administering the composition to the first transgenic rat; and (d) comparing the phenotype of the first transgenic rat to which the composition was administered with the phenotype of the second transgenic rat in which the composition was not administered, wherein any less extensive development in the nature or extent of the phenotype in the first transgenic rat or any increased length of time required for the phenotype to develop in the first transgenic rat that has been administered the composition relative to the phenotype in the second transgenic rat, indicates the potential of the composition to counteract degradation of Type II collagen in joints.

29. The transgenic rat of claim 20, wherein the transcription activator protein is a chimeric polypeptide comprising a transactivator domain linked to a progesterone receptor ligand-binding domain.

30. A method for producing degradation of Type II collagen in the joints of a transgenic rat, which method comprises:

(a) maintaining the transgenic rat of claim 29 in the absence of mifepristone (RU 486) until adulthood; and (b) activating expression of the matrix metalloproteinase in the transgenic rat by administering mifepristone (RU 486) to the rat after the rat has reached adulthood such that the matrix metalloproteinase degrades Type II collagen in the joints of the rat.

31. The method according to claim 30, wherein the Type II collagen degradation results in a loss of proteoglycan, cleavage of type II collagen into a TCA degradation product, a change in joint function, joint space narrowing, destruction of cartilage, a change in growth plate morphology, fibrillation and loss of articular cartilage, osteophyte formation, or combinations thereof.

32. A method for evaluating the potential of a composition to counteract degradation of Type II collagen in joints of a transgenic rat, which degradation results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:

(a) providing a first and second transgenic rat of claim 29;

(b) activating expression of the metalloproteinase at the same age during adulthood of the transgenic rats, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;

(c) administering the composition to the first transgenic rat; and (d) comparing the phenotype of the first transgenic rat to which the composition was administered with the phenotype of the second transgenic rat in which the composition was not administered, wherein any less extensive development in the nature or extent of the phenotype in the first transgenic rat or any increased length of time required for the phenotype to develop in the first transgenic rat that has been administered the composition relative to the phenotype in the second transgenic rat, indicates the potential of the composition to counteract degradation of Type II collagen in joints.

33. The transgenic rat of claim 20, wherein the transcription activator protein is a chimeric polypeptide comprising a transactivator domain linked to a steroid binding domain.

34. A method for evaluating the potential of a composition to counteract degradation of Type II collagen in joints of a transgenic rat, which degradation results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:

(a) providing a first and second transgenic rat of claim 33;

(b) activating expression of the metalloproteinase at the same age during adulthood of the rats, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;

(c) administering the composition to the first transgenic rat; and (d) comparing the phenotype of the first transgenic rat to which the composition was administered with the phenotype of the second transgenic rat in which the composition was not administered, wherein any less extensive development in the nature or extent of the phenotype in the first transgenic rat or any increased length of time required for the phenotype to develop in the first transgenic rat that has been administered the composition relative to the phenotype in the second transgenic rat, indicates the potential of the composition to counteract degradation of Type II collagen in joints.

35. A method for producing degradation of Type II collagen in the joints of a transgenic rat, which method comprises:

(a) maintaining the transgenic rat of claim 33 in the absence of mifepristone (RU 486) until adulthood; and (b) activating expression of the matrix metalloproteinase in the transgenic rat by administering mifepristone (RU 486) to the rat after the rat has reached adulthood such that the matrix metalloproteinase degrades Type II collagen in the joints of the rat.

36. The transgenic rat of claim 20, wherein the Type II collagen degradation results in a loss of proteoglycan, cleavage of type II collagen into a TCA degradation product, a change in joint function, joint space narrowing, destruction of cartilage, a change in growth plate morphology, fibrillation and loss of articular cartilage, osteophyte formation, or combinations thereof.

37. A method for producing degradation of Type II collagen in the joints of a transgenic non-human rat, which method comprises:

(a) maintaining the transgenic rat of claim 20 in the absence of the transcription activator protein-binding compound until adulthood; and (b) activating expression of the matrix metalloproteinase in the transgenic rat by administering the compound to the rat after the rat has reached adulthood such that the matrix metalloproteinase degrades Type II collagen in the joints of the rat.

38. A method for evaluating the potential of a composition to counteract degradation of Type II collagen in joints of a transgenic rat, which degradation results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:

(a) providing a first and second transgenic rat of claim 20;

(b) activating expression of the metalloproteinase at the same age during adulthood of the transgenic rats, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;

(c) administering the composition to the first transgenic rat; and (d) comparing the phenotype of the first transgenic rat to which the composition was administered with the phenotype of the second transgenic rat in which the composition was not administered, wherein any less extensive development in the nature or extent of the phenotype in the first transgenic rat or any increased length of time required for the phenotype to develop in the first transgenic rat that has been administered the composition relative to the phenotype in the second transgenic rat, indicates the potential of the composition to counteract degradation of Type II collagen in joints.

39. A method for evaluating the potential of a composition to counteract degradation of Type II collagen in joints of a transgenic mouse, which degradation results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof, which method comprises:
  (a) providing a first and second transgenic mouse, whose genomes each comprise:
    (i) a nucleotide sequence encoding a constitutively enzymatically active human matrix metalloproteinase that cleaves Type II collagen, wherein the nucleotide sequence encoding the metalloproteinase is operatively linked to a regulatable promoter; and
    (ii) a nucleotide sequence encoding a repressor-activator fusion polypeptide that binds to the regulatable promoter in the absence of a repressor-activator fusion polypeptide-binding compound and does not bind to the regulatable promoter in the presence of the compound, which nucleotide sequence encoding the repressor-activator fusion polypeptide is operatively linked to a chondrocyte-specific promoter,
  wherein expression of the metalloproteinase is capable of being repressed in the mouse until adulthood, and wherein the metalloproteinase is capable of being expressed in the mouse during adulthood to a level sufficient to cause Type II collagen degradation in the joints of the mouse;
  (b) activating expression of the metalloproteinase at the same age during adulthood of the transgenic mice, wherein expression of the metalloproteinase results in a phenotypic change selected from the group consisting of loss of proteoglycan, cleavage of Type II collagen into a TCA degradation product, a change in joint function, joint space narrowing, destruction of cartilage, a change in growth plate morphology, fibrillation and loss of articular cartilage, osteophyte formation, and combinations thereof;
  (c) administering the composition to the first transgenic mouse; and
  (d) comparing the phenotype of the first transgenic mouse to which the composition was administered with the phenotype of the second transgenic mouse in which the composition was not administered,
  wherein any less extensive development in the nature or extent of the phenotype in the first transgenic mouse or any increased length of time required for the phenotype to develop in the first transgenic mouse that has been administered the composition relative to the mouse phenotype in the second transgenic mouse, indicates the potential of the composition to counteract degradation of Type II collagen in joints.

40. The method of claim 39, wherein the repressor-activator fusion polypeptide of the transgenic mouse is a chimeric tetracycline repressor-VP16 transcription activator polypeptide and the regulatable promoter is a Tn10 sequence linked to a portion of the CMV IE promoter.

41. The method of claim 39, wherein the regulatable promoter is a tetracycline-regulatable promoter and the repressor-activator fusion polypeptide-binding compound is tetracycline or a tetracycline analog.

* * * * *